United States Patent
Yang

(10) Patent No.: US 8,106,046 B2
(45) Date of Patent: Jan. 31, 2012

(54) CYCLOPENTATHIOPHENE MODULATORS OF THE GLUCOCORTICOID RECEPTOR, AP-1, AND/OR NF-κB ACTIVITY AND USE THEREOF

(75) Inventor: Bingwei Vera Yang, Belle Mead, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 12/996,806

(22) PCT Filed: Jun. 24, 2009

(86) PCT No.: PCT/US2009/048396
§ 371 (c)(1),
(2), (4) Date: Dec. 8, 2010

(87) PCT Pub. No.: WO2009/158380
PCT Pub. Date: Dec. 30, 2009

(65) Prior Publication Data
US 2011/0105495 A1    May 5, 2011

Related U.S. Application Data

(60) Provisional application No. 61/075,063, filed on Jun. 24, 2008.

(51) Int. Cl.
C07D 413/14 (2006.01)
C07D 417/12 (2006.01)
A61K 31/433 (2006.01)
A61K 31/5377 (2006.01)
A61P 19/02 (2006.01)
A61P 29/00 (2006.01)

(52) U.S. Cl. ............ 514/232.8; 514/363; 544/134; 548/136; 548/139

(58) Field of Classification Search .......... None
See application file for complete search history.

(56) References Cited

U.S. PATENT DOCUMENTS 4,649,153 A * 3/1987 Ferrand et al. .......... 514/443
7,105,562 B2   9/2006 Zhang et al.

FOREIGN PATENT DOCUMENTS

| WO | WO 92/03434 | 3/1992 |
| WO | WO 02/28820 | 4/2002 |
| WO | WO 2008/057855 | 5/2008 |

OTHER PUBLICATIONS

Golub et al., Science, vol. 286, Oct. 15, 1999, pp. 531-537.*
Bonini, B.-F. et al., "Cyclopenta[b]thiophene-alkyloxazolines: new nitrogen-sulfur hybrid ligands and their use in asymmetric palladium-catalyzed allylic alkylation", Tetrahedron: Asymmetry, vol. 15, No. 6, pp. 1043-1051 (2004).
Kawatsura, M. et al., "Iron(III) Chloride Catalyzed Nazarov Cyclization of 3-Substituted Thiophene Derivatives", Synlett, No. 7, pp. 1009-1012 (2008).

* cited by examiner

*Primary Examiner* — Fiona T Powers
(74) *Attorney, Agent, or Firm* — Burton Rodney

(57) ABSTRACT

A compound of Formula (I) and enantiomers, diastereomers and pharmaceutically-acceptable salts thereof, wherein $R^1$, $R^2$, $R^3$, $R^4$, $R^5$, $R^6$, $R^7$ and $R^8$ are as defined herein. Also disclosed are pharmaceutical compositions and combinations containing compounds of Formula I and methods of treating diseases or disorders including metabolic and inflammatory or immune associated diseases or disorders.

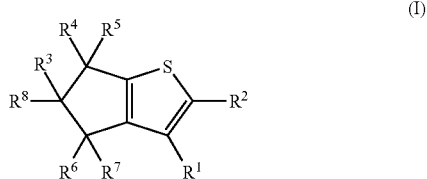

10 Claims, No Drawings

CYCLOPENTATHIOPHENE MODULATORS OF THE GLUCOCORTICOID RECEPTOR, AP-1, AND/OR NF-κB ACTIVITY AND USE THEREOF

This application claims priority from U.S. Provisional Application 61/075,063 filed Jun. 24, 2008, which is incorporated herein by reference.

FIELD OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions thereof and methods for using such compounds and compositions to treat these and related diseases or disorders.

BACKGROUND OF THE INVENTION

Transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation*, 107:3 (2001); Firestein, G. S. et al., *Arthritis and Rheumatism*, 42:609 (1999); and Peltz, G., *Curr. Opin. in Biotech.*, 8:467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. et al., *Nature Rev. Drug Disc.*, 2:554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.*, 6(5):720-728 (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228:740-742 (1985); Weinberger et al., *Nature*, 318:670-672 (1986) and for results in rats see Miesfeld, R., *Nature*, 312:779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62:1189 (1990); Yang-Yen, H. F. et al., *Cell*, 62:1205 (1990); Diamond, M. I. et al., *Science*, 249:1266 (1990); and Caldenhoven, E. et al., *Mol. Endocrinol.*, 9:401 (1995). Other mechanisms such as sequestration of co-activators by GR have also been proposed. See Kamei, Y. et al., *Cell*, 85:403 (1996); and Chakravarti, D. et al., *Nature*, 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR.

These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93:531 (1998) and Reichardt, H. M., *EMBO J.*, 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions and combinations thereof and methods for using such compounds, combinations and compositions to treat these and related diseases or disorders.

In accordance with one aspect of the invention (Embodiment 1), compounds are provided having the structure of Formula I,

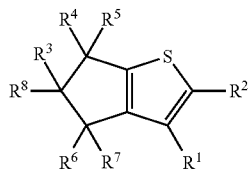

I or an isotope, enantiomer, diastereomer, or a pharmaceutically-acceptable salt thereof, wherein:

$R^1$ and $R^2$ are independently selected from the group consisting of: hydrogen, halogen, alkyl, substituted alkyl, alkenyl, substituted alkenyl, alkynyl, substituted alkynyl, nitro, azido, cyano, $OR^{10}$, $NR^{10}R^{11}$, $—(O)_t—C(=O)R^{10}$, $—(O)_t—CO_2R^{10}$, $—(O)_t—C(=O)NR^{10}R^{11}$, $NR^{10}C(=O)R^{11}$, $NR^{10}C(=O)OR^{11}$, $NR^{10}C(=S)OR^{11}$, $S(=O)_pR^{15}$ $NR^{11}S(=O)_pR^{15}$, $N(S(=O)_pR^{15})_2$, $S(=O)_pNR^{10}R^{11}$, cycloalkyl, substituted cycloalkyl, cycloalkenyl, substituted cycloalkenyl, heterocyclo, substituted heterocyclo, aryl, substituted aryl, heteroaryl and substituted heteroaryl;

at least one of $R^3$, $R^4$, $R^5$, $R^6$, $R^7$ and $R^8$ is $R^9—NH—C(=O)$ and the rest are independently selected from the group consisting of: hydrogen, halogen, alkyl, substituted alkyl, alkenyl, substituted alkenyl, alkynyl, substituted alkynyl, nitro, cyano, $OR^{12}$, $SR^{12}$, $NR^{12}R^{13}$, $C(=O)R^{12}$, $CO_2R^{12}$, $C(=O)NR^{12}R^{13}$, $—O—C(=O)R^{12}$, $NR^{12}C(=O)R^{13}$, $NR^{12}C(=O)OR^{13}$, $NR^{12}C(=S)OR^{13}$, $S(=O)_pR^{16}$, $NR^{12}S(=O)_pR^{16}$, $S(=O)_pNR^{12}R^{13}$, cycloalkyl, substituted cycloalkyl, cycloalkenyl, substituted cycloalkenyl, heterocyclo, substituted heterocyclo, aryl, substituted aryl, heteroaryl and substituted heteroaryl;

$R^9$ is selected from the group consisting of: hydrogen, $C_{1-6}$alkyl, $OR^{14}$, substituted $C_{1-6}$alkyl, cycloalkyl, substituted cycloalkyl, aryl, substituted aryl, heterocyclo, substituted heterocyclo, heteroaryl and substituted heteroaryl;

$R^{10}$, $R^{11}$, $R^{12}$, $R^{13}$ and $R^{14}$ at each occurrence are independently selected from the group consisting of: (i) hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclo and substituted heterocyclo; or (ii) together with the atoms to which they are attached, $R^{10}$ is combined with $R^{11}$ and/or $R^{12}$ is combined with $R^{13}$ to form a heteroaryl or heterocyclo ring;

$R^{15}$ and $R^{16}$ at each occurrence are independently selected from the group consisting of: alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclo and substituted heterocyclo;

t at each occurrence is 0 or 1; and p at each occurrence is 1 or 2.

Other embodiments of the present invention are as described below.

Embodiment 2 a compound as defined in Embodiment 1, or an isotope, enantiomer, diastereomer, tautomer, or a pharmaceutically acceptable salt thereof, where one of $R^1$ or $R^2$ is hydrogen and the other is selected from the group consisting of: halogen, cyano, alkyl, substituted alkyl, alkenyl, substituted alkenyl, alkynyl, substituted alkynyl, cycloalkyl, substituted cycloalkyl, cycloalkenyl, substituted cycloalkenyl, heterocyclo, substituted heterocyclo, aryl, substituted aryl, heteroaryl and substituted heteroaryl.

Embodiment 3 a compound as defined in Embodiments 1-2, or an enantiomer, diastereomer, tautomer, or a pharmaceutically acceptable salt thereof, where one of $R^1$ and $R^2$ is hydrogen and the other is selected from heterocyclo, substituted heterocyclo, aryl, substituted aryl, heteroaryl and substituted heteroaryl.

Embodiment 4 a compound as defined in Embodiment 1-3, or an enantiomer, diastereomer, tautomer, or a pharmaceutically acceptable salt thereof, where one of $R^1$ or $R^2$ is hydrogen and the other is selected from the group consisting of: unsubstituted phenyl and phenyl substituted with one to two groups selected from halogen, morpholin-1-ylcarbonyl, pyrrolidin-1-ylcarbonyl, N-methyl-N-ethylaminocarbonyl, 3-fluoropyrrolidin-1-ylcarbonyl, 3,3-difluoropyrrolidin-1-ylcarbonyl and N,N-dimethylaminocarbonyl.

Embodiment 5 a compound as defined in Embodiments 1-4, or an enantiomer, diastereomer, tautomer, or a pharmaceutically acceptable salt thereof, where one of $R^1$ and $R^2$ is hydrogen and the other is a halogen. Preferably the halogen is selected from fluorine, bromine or chlorine.

Embodiment 6 a compound as defined in Embodiments 1-5, or an enantiomer, diastereomer, tautomer, or a pharmaceutically acceptable salt thereof, wherein $R^8$ is $R^9—NH—C(=O)$.

Embodiment 7 a compound as defined in Embodiments 1-6, or an enantiomer, diastereomer, tautomer, or a pharmaceutically acceptable salt thereof, where $R^9$ is selected from aryl, substituted aryl, heterocyclo, substituted heterocyclo, heteroaryl and substituted heteroaryl.

Embodiment 8 a compound as defined in Embodiments 1-7, or an enantiomer, diastereomer, tautomer, or a pharmaceutically acceptable salt thereof, where $R^9$ is:

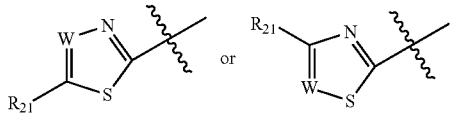

wherein:
W is $CR^{22}$ or N; and
$R^{21}$ and $R^{22}$ are independently selected from the group consisting of hydrogen, halogen, lower alkyl, cyano, $CF_3$, (lower alkyl)amino, cyano, (lower alkyl)sulfonyl, ($C_{3-5}$ cycloalkyl)carboxamide, and (lower alkyl)$_{1-2}$carboxamide.

Embodiment 9 a compound as defined in Embodiments 1-8, or an enantiomer, diastereomer, tautomer, or a pharmaceutically acceptable salt thereof, wherein $R^8$ is $R^9$—NH—C(=O) and $R^9$ is a thiadiazolyl group (optionally substituted). Preferably the thiadiazolyl group is 1,3,5-thidiazol-2-yl, 1,3,4-thiadiazol-2-yl or thiazol-2-yl, and especially 1,3,4-thiadiazol-2-yl.

Embodiment 10 a compound as defined in Embodiments 1-9, or an enantiomer, diastereomer, tautomer, or a pharmaceutically acceptable salt thereof, wherein:
one of $R^1$ or $R^2$ is hydrogen, lower alkyl or cyano, and the other of $R^1$ or $R^2$ is halogen or phenyl substituted with one to two groups selected from halogen, (optionally substituted, 5- to 7-membered)heterocyclocarbonyl, and (lower alkyl)$_{1-2}$aminocarbonyl.
$R^3$ is lower alkyl, cyano, $NH_2$, (lower alkyl)$_{1-2}$amino, $CF_3$ or benzyl; and
$R^4$, $R^5$, $R^6$ and $R^7$ are hydrogen, lower alkyl, optionally substituted phenyl, or optionally substituted 5 or 6-membered heteroaryl, wherein the optionally substituted substituents are selected from the group consisting of: halogen, lower alkyl, cyano, $CF_3$, (lower alkyl)amino, cyano, (lower alkyl)sulfonyl and carboxamide, provided that one and only one of $R^4$, $R^5$, $R^6$ and $R^7$ is selected from optionally substituted phenyl or optionally substituted 5- to 7-membered heteroaryl.

Embodiment 11 a compound as defined in Embodiments 1-10, or an enantiomer, diastereomer, tautomer, or a pharmaceutically acceptable salt thereof, wherein:
one of $R^1$ or $R^2$ is hydrogen and the other is phenyl substituted with one to two groups selected from halogen, morpholin-1-ylcarbonyl, pyrrolidin-1-ylcarbonyl, N-methyl-N-ethylaminocarbonyl, 3,3-difluoropyrrolidin-1-ylcarbonyl and N,N-dimethylaminocarbonyl;
$R^3$ is lower alkyl (preferably methyl);
$R^4$ is hydrogen;
$R^5$ is hydrogen;
$R^6$ is phenyl or phenyl substituted with a halogen;
$R^7$ is hydrogen; and
$R^9$ is 1,3,5-thidiazol-2-yl, 1,3,4-thiadiazol-2-yl or thiazol-2-yl, each group optionally substituted with one to two groups selected from halogen, lower alkyl, cyano, $CF_3$, (lower alkyl)$_{1-2}$amino, cyano, (lower alkyl)sulfonyl, ($C_{3-5}$ cycloalkyl)carboxamide and (lower alkyl)$_{1-2}$carboxamide.

Embodiment 12 a compound as defined in Embodiments 1-11, or an enantiomer, diastereomer, tautomer, or a pharmaceutically acceptable salt thereof, wherein:
$R^8$ is $R^9$—NH—C(=O); and
$R^3$ is selected from hydrogen, halogen, alkyl, substituted alkyl, alkenyl, substituted alkenyl, alkynyl, substituted alkynyl, nitro, cyano, $OR^{12}$, $SR^{12}$, $NR^{12}R^{13}$, $C(=O)R^{12}$, $CO_2R^{12}$, $C(=O)NR^{12}R^{13}$, —O—C(=O)$R^{12}$, $NR^{12}C(=O)R^{13}$, $NR^{12}C(=O)OR^{13}$, $NR^{12}C(=S)OR^{13}$, $S(=O)_pR^{16}$, $NR^{12}S(=O)_pR^{16}$, $S(=O)_pNR^{12}R^{13}$, cycloalkyl, substituted cycloalkyl, cycloalkenyl, substituted cycloalkenyl, heterocyclo, substituted heterocyclo, aryl, substituted aryl, heteroaryl and substituted heteroaryl.

Embodiment 13 a compound as defined in Embodiments 1-12, or an enantiomer, diastereomer, tautomer, or a pharmaceutically acceptable salt thereof, wherein:
one of $R^1$ or $R^2$ is hydrogen and the other is phenyl substituted in the 4-position with morpholin-1-ylcarbonyl, pyrrolidin-1-ylcarbonyl, N-methyl-N-ethylaminocarbonyl, 3-fluoropyrrolidin-1-ylcarbonyl, 3,3-difluoropyrrolidin-1-ylcarbonyl or N,N-dimethylaminocarbonyl, and optionally, halogen.

Embodiment 14 a compound as defined in Embodiments 1-13, or an enantiomer, diastereomer, tautomer, or a pharmaceutically acceptable salt thereof, where $R^3$ is lower alkyl, especially methyl.

Embodiment 15 a compound as defined in Embodiments 1-14, or an enantiomer, diastereomer, tautomer, or a pharmaceutically acceptable salt thereof, wherein:
$R^4$ is selected from hydrogen, halogen, alkyl, substituted alkyl, alkenyl, substituted alkenyl, alkynyl, substituted alkynyl, cycloalkyl, substituted cycloalkyl, cycloalkenyl, substituted cycloalkenyl, heterocyclo and substituted heterocyclo;
$R^5$ is selected from aryl, substituted aryl, heteroaryl, substituted heteroaryl, halogen, alkyl, substituted alkyl, alkenyl, substituted alkenyl, alkynyl, substituted alkynyl, cycloalkyl, substituted cycloalkyl, cycloalkenyl, substituted cycloalkenyl, heterocyclo and substituted heterocyclo; and
$R^6$ and $R^7$, are independently selected from hydrogen, halogen, alkyl, substituted alkyl, alkenyl, substituted alkenyl, alkynyl, substituted alkynyl, nitro, cyano, $OR^9$, $NR^9R^{10}$, —(O)$_t$—C(=O)$R^9$, —(O)$_t$—CO$_2R^9$, —(O)$_t$—C(=O)NR$^9R^{10}$, $NR^9C(=O)R^{10}$, $NR^9C(=O)OR^{10}$, $NR^9C(=S)OR^{10}$, $S(=O)_pR^{14}_qR^{14}$, $NR^{10}S(=O)_pR^{14}$, $N(S(=O)_pR^{14})_2$, $S(=O)_pNR^9R^{10}$, cycloalkyl, substituted cycloalkyl, cycloalkenyl, substituted cycloalkenyl, heterocyclo, substituted heterocyclo, aryl, substituted aryl, heteroaryl and substituted heteroaryl.

Embodiment 16 a pharmaceutical composition including at least one compound according to Embodiments 1-15 and a pharmaceutically-acceptable carrier.

Embodiment 17 a method of treating a disease or disorder selected from the group consisting of: inflammatory disease, immune disease and metabolic disease, comprising administering to a patient in need of treatment, a therapeutically effective amount of a compound according to Embodiments 1-16.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of Formula I, or an enantiomer, diastereomer, or a pharmaceutically-acceptable salt, and a pharmaceutically acceptable carrier therefore.

Other embodiments of the present invention are 1) a method of treating a disease or disorder comprising administering to a patient in need of treatment a therapeutically effective amount of a compound of Formula I, 2) a compound of Formula I for use in treating a disease or disorder, and 3) use of a compound of Formula I in the manufacture of a medicament for treatment of a disease or disorder, wherein the disease or disorder is selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease.

Other embodiments of the present invention are 1) a method of treating a disease or disorder comprising administering to a patient in need of treatment a therapeutically effective amount of a compound of Formula I, 2) a compound of Formula I for use in treating a disease or disorder, and 3) use of a compound of Formula I in the manufacture of a medicament for treating a disease or disorder wherein the disease or disorder is selected from a metabolic disease or an inflammatory or immune disease comprising the administration to a patient in need of treatment, a therapeutically effective amount of a compound of Formula I.

A more preferred embodiment of the present invention provides 1) a method of treating a disease or disorder comprising administering to a patient in need of treatment a therapeutically effective amount of a compound of Formula I, 2) a compound of Formula I for use in treating a disease or disorder, and 3) use of a compound of Formula I in the manufacture of a medicament for treating a disease or disorder wherein the disease or disorder is selected from a metabolic disease wherein the disease is selected from Type I diabetes, Type II diabetes, juvenile diabetes, and obesity.

Other preferred embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is an inflammatory or immune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosus, myasthenia gravis, psoriasis, dermatitis, dermatomyositis, eczema, seborrhea, pulmonary inflammation, eye uveitis, hepatitis, Graves' disease, Hashimoto's thyroiditis, autoimmune thyroiditis, Behcet's or Sjorgren's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, alveolitis, contact hypersensitivity, delayed-type hypersensitivity, contact dermatitis, urticaria, skin allergies, respiratory allergies, hayfever, gluten-sensitive enteropathy, osteoarthritis, acute pancreatitis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anaemia, leukemias and lymphomas in adults, acute leukemia of childhood, regional enteritis, autoimmune vasculitis, sepsis, and chronic obstructive pulmonary disease.

Especially preferred embodiments are 1) a method of treating a disease or disorder comprising administering to a patient in need of treatment a therapeutically effective amount of a compound of Formula I, 2) a compound of Formula I for use in treating a disease or disorder, and 3) use of a compound of Formula I in the manufacture of a medicament for treating a disease or disorder where the disease or disorder is selected from transplant rejection, rheumatoid arthritis, psoriatic arthritis, multiple sclerosis, asthma, inflammatory bowel disease, systemic lupus erythematosis, and psoriasis.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

In still another embodiment, the present invention provides a pharmaceutical combination comprising one or more compounds of Formula I and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fabric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker, as a medicament for the treatment of a condition, for sequential or concurrent use.

Even more preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid_lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary adrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger, et al., *Science,* 228:740-742 (1985), and in Weinberger, et al., *Nature,* 318:670-672 (1986); rat glucocorticoid receptor as disclosed in Miesfeld, R., *Nature,* 312:779-781 (1985); mouse glucocorticoid receptor as disclosed in Danielson, M. et al., *EMBO J.,* 5:2513; sheep glucocorticoid receptor as disclosed in Yang, K. et al., *J. Mol. Endocrinol.,* 8:173-180 (1992); marmoset glucocorticoid receptor as disclosed in Brandon, D. D. et al., *J. Mol. Endocrinol.* 7:89-96 (1991); and human GR-beta as disclosed in Hollenberg, S. M. et al., *Nature,* 318:635 (1985); Bamberger, C. M. et al., *J. Clin. Invest.,* 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhea, pulmonary inflammation, eye uveitis, hepatitis, Graves' disease, Hashimoto's thyroiditis, autoimmune thyroiditis, Behcet's or Sjorgren's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (regimentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), urticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and/or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. The term "lower alkyl" refers to alkyl groups of 1 to 4 carbon atoms and are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —N(alkyl)$_3^+$, —$NR_aSO_2$, —$NR_aSO_2R_c$, —$SO_2R_c$ —$SO_2NR_aR_b$, —$SO_2NR_aC$(=O) $R_b$, $SO_3H$, —$PO(OH)_2$, —OC(=O)$R_a$, —C(=O)$R_a$, —$CO_2R_a$, —C(=O)$NR_aR_b$, —C(=O)($C_{1-4}$alkylene) $NR_aR_b$, —C(=O)$NR_a(SO_2)R_b$, —$CO_2(C_{1-4}$alkylene) $NR_aR_b$, —$NR_aC$(=O)$R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2$(alkyl), $C_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, =O (as valence allows), $CF_3$, O($C_{1-6}$alkyl), $OCF_3$, C(=O)H, C(=O)($C_{1-6}$alkyl), $CO_2H$, $CO_2(C_{1-6}$alkyl), $NHCO_2(C_{1-6}$ alkyl), —S($C_{1-6}$alkyl), —$NH_2$, NH($C_{1-6}$alkyl), N($C_{1-6}$ alkyl)$_2$, N($CH_3$)$_3^+$, $SO_2(C_{1-6}$alkyl), C(=O)($C_{1-4}$alkylene) $NH_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four to seven membered heterocyclo or cycloalkyl, or a five to six membered heteroaryl. When a substituted alkyl is substituted with an aryl (including, for example, phenyl and napthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

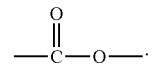

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—($CH_2$)$_{1-5}$NH—$CH_2$—, —O—($CH_2$)$_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2\text{-}3}$heteroalkylene, the subscript refers to the number of carbon atoms in the group in addition to heteroatoms. Thus, for example, a $C_{1\text{-}2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1\text{-}2}$alkylene, or $C_{2\text{-}3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; $A_2$ is a bond, $C_{1\text{-}3}$alkylene, $C_{2\text{-}3}$alkenylene, —C$_{1\text{-}4}$alkylene-NR$_d$—, —C$_{1\text{-}4}$alkylene-NR$_d$C(=O)—, —C$_{1\text{-}4}$alkylene-S—, —C$_{1\text{-}4}$alkylene-SO$_2$—, or —C$_{1\text{-}4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—$C_{1\text{-}6}$alkyl.

The term "alkylthio" refers to a sulfur atom that is substituted by an alkyl or substituted alkyl group as defined herein. For example, the term "thioalkyl" includes the group —S—$C_{1\text{-}6}$alkyl, and so forth.

The term "alkylamino" refers to an amino group substituted with an alkyl group or substituted alkyl group as defined above. For example, the term "alkylamino" includes the group —NR—$C_{1\text{-}12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent $C_{1\text{-}2}$aminoalkyl includes the groups —CH$_2$—N(CH$_3$)$_2$, and —(CH$_2$)$_2$—NH$_2$. A lower aminoalkyl comprises an aminoalkyl having one to four carbon atoms. The term ($C_{1\text{-}4}$alkyl)$_{0\text{-}2}$amino includes the groups NH$_2$, —NH($C_{1\text{-}4}$alkyl), and —N($C_{1\text{-}4}$alkyl)$_2$. "Amino" used by itself refers to the group NH$_2$. A "substituted amino" refers to an amino group substituted as described above for the nitrogen atom of a heteroalkylene chain and includes, for example, the terms alkylamino and acylamino (—NR$_d$C(=O)R$_e$). Where amino is designated as mono-substituted without further definition, the extra nitrogen valence is hydrogen.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1\text{-}12}$alkyl, whereas a bivalent alkoxy includes groups such as —O—$C_{1\text{-}12}$alkylene-.

It should be understood that the selections for all groups, including for examples, alkoxy, thioalkyl, and aminoalkyl, will be made by one skilled in the field to provide stable compounds. Thus, for example, in compounds of Formula I, when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is a heterocyclo group, including, without limitation, morpholinyl or pyrrolidinyl.

The term "acyl" refers to a carbonyl group linked to an organic radical, more particularly, the group C(=O)R$_e$. The group R$_e$ can be selected from alkyl, alkenyl, alkynyl, aminoalkyl, substituted alkyl (i.e., substituted alkylene), substituted alkenyl, substituted alkynyl, cycloalkyl, heterocyclo, aryl, or heteroaryl, as defined herein. When R$_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

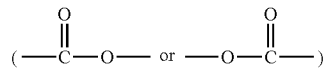

linked to an organic radical (CO$_2$R$_e$), as well as the bivalent groups —CO$_2$—, —CO$_2$R$_e$— which are linked to organic radicals in compounds of Formula I, wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of Formula I, when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "sulfonyl" refers to a sulphoxide group (—S(=O)$_2$—) linked to an organic radical in compounds of Formula I, more particularly, the monovalent group —S(=O)$_2$—R$_e$. Likewise, the term "sulfinyl" refers to the group (—S(=O)—) linked to an organic radical in compounds of Formula I, more particularly, the monovalent group —S(=O)—R$_e$. Additionally, the sulfonyl or sulfinyl group may be bivalent, in which case R$_e$ is a bond. The group R$_e$ is selected from those recited above for acyl and alkoxycarbonyl groups, with the exception that R$_e$ is not hydrogen.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$ —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$ alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Accordingly, in compounds of Formula I, the term "cycloalkyl" includes cyclopropyl, cyclobutyl, cyclopentyl, cyclohexyl, cycloheptyl, bicyclooctyl, etc., as well as the following ring systems,

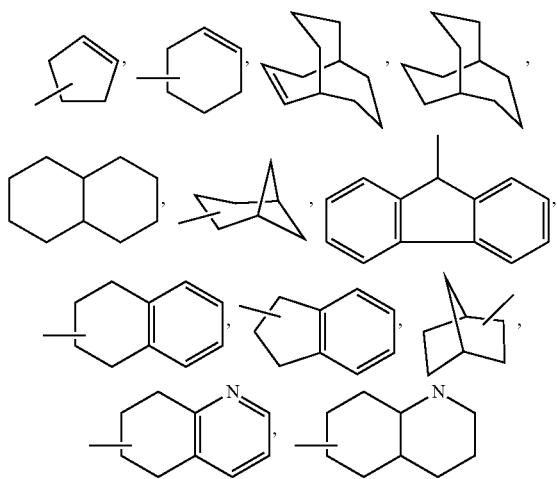

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), SO$_3$H, —NR$_a$R$_b$, —N(alkyl)$_3^+$, —NR$_a$SO$_2$, —NR$_a$SO$_2$R$_c$, —SO$_2$R$_c$ —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Thus, examples of aryl groups include:

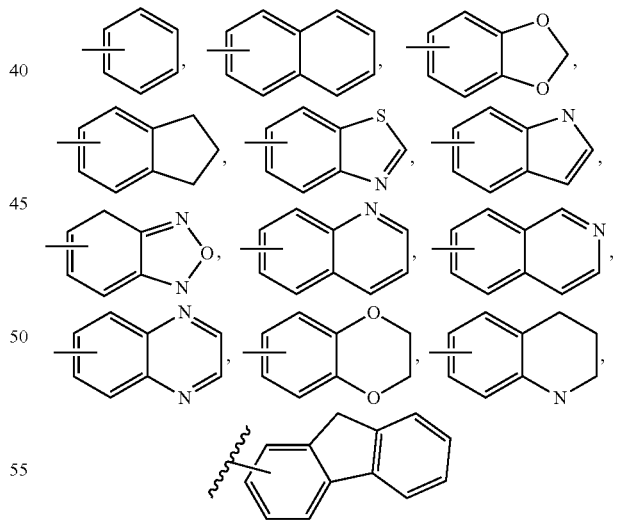

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Heterocyclo groups in compounds of Formula I include

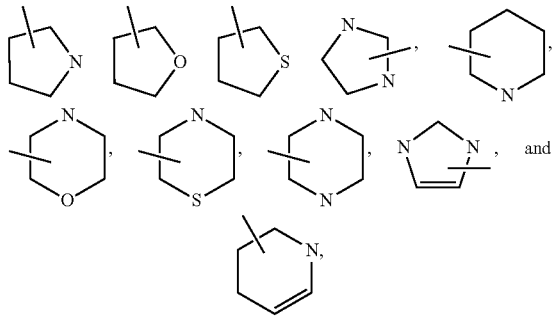

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4} alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of Formula I, preferred heteroaryl groups include

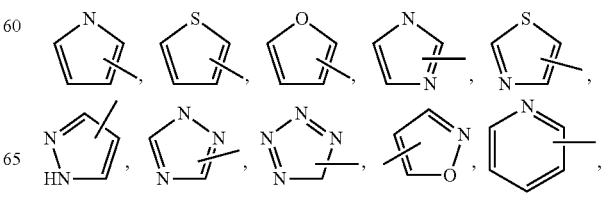

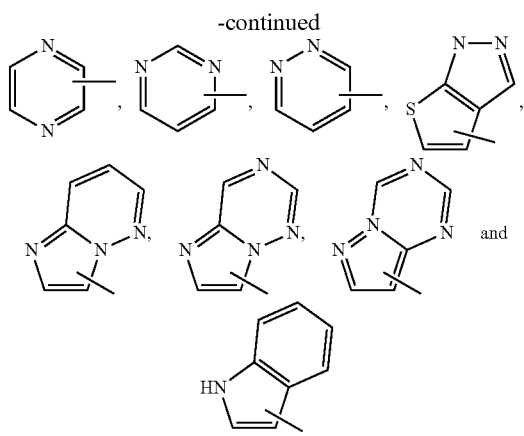

and the like, which optionally may be substituted at any available carbon or nitrogen atom. Aromatic rings may also be designated by an unbroken circle in the ring.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

The compounds of Formula I can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of Formula I contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the Formula I may be formed, for example, by reacting a compound of the Formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates (e.g., hydrates) of the inventive compounds are also contemplated. The term "prodrug" denotes a compound which, upon administration to a subject, undergoes chemical conversion by metabolic or chemical processes to yield a compound of the Formula I, and/or a salt and/or solvate thereof. Any compound that will be converted in vivo to provide the bioactive agent (i.e., the compound for Formula I) is a prodrug within the scope and spirit of the invention. For example, compounds containing a carboxy group can form physiologically hydrolyzable esters which serve as prodrugs by being hydrolyzed in the body to yield Formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the Formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

Utilities and Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of Formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of Formula I of the invention include azathiprine, 5-fluorouracil, cyclophosphamide, cisplatin, methotrexate, thiotepa, carboplatin, and the like.

The anti-viral agents which may be optionally employed in combination with compounds of Formula I of the invention include abacavir, aciclovir, ganciclovir, zidanocin, vidarabine, and the like.

The anti-inflammatory agents which may be optionally employed in combination with compounds of Formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g., CD40Ig and CD8gp39), inhibitors, such as nuclear translocation inhibitors, of NF-kappa B function, such as deoxyspergualin (DSG).

The anti-fungal agents which may be optionally employed in combination with compounds of Formula I of the invention include fluconazole, miconazole, amphotericin B, and the like.

The antibiotics which may be optionally employed in combination with compounds of Formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of Formula I of the invention include methotrexate, leflunomide, FK506 (tacrolimus, Prograf).

The hypolipidemic agent or lipid-lowering agent or lipid modulating agents which may be optionally employed in combination with the compounds of Formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, and 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135, 5,712,279, and 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

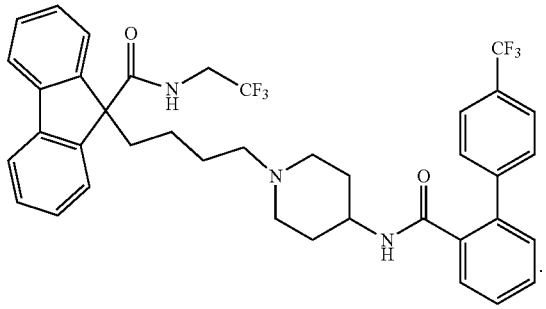

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987), and cyclopropanes reported by Capson, T. L., PhD dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, *Drugs of the Future*, 24:9-15 (1999), (Avasimibe); Nicolosi et al., "The ACAT inhibitor, C1-1011 is effective in the prevention and regression of aortic fatty streak area in hamsters", *Atherosclerosis* (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al, "ACAT inhibitors: potential anti-atherosclerotic agents", *Curr. Med. Chem.* 1(3):204-25 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", *Chemtracts: Org. Chem.*, 8(6):359-362 (1995), or TS-962 (acetamide, N-[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis*, 115:45-63 (1995) and *J. Med. Chem.*, 41:973 (1998).

The hypolipidemic agent may be an ileal Na+/bile acid cotransporter inhibitor such as disclosed in *Drugs of the Future,* 24:425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physicians' Desk Reference and/or in the patents set out above.

The compounds of Formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacology,* 120:1199-1206 (1997), and Cornicelli et al, "15-Lipoxygenase and its Inhibition: A Novel Therapeutic Target for Vascular Disease", *Current Pharmaceutical Design,* 5:11-20 (1999).

The compounds of Formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of Formula I may be 1, 2, 3 or more antidiabetic agents or antihyperglycemic agents including insulin secretagogues or insulin sensitizers, or other antidiabetic agents preferably having a mechanism of action different from the compounds of Formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-

1,4-bis-4-[(3,5-dioxo-1,2,4-oxadiazolidin-2-yl-methyl)]phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1-36) amide, GLP-1 (7-36) amide, GLP-1 (7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614, 492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2, 4-dioxo-5-thiazolidinyl)methyl]-2-methoxy-N-[[4-(trifluoromethyl)phenyl]methyl]-(Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", *Diabetes*, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), saxagliptin (preferred), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., *Biochemistry*, 38(36):11597-11603, (1999), TSL-225 (tryptophyl-1,2,3,4-tetrahydro-isoquinoline-3-carboxylic acid (disclosed by Yamada et al., *Bioorg. & Med. Chem. Leu.*, 8:1537-1540 (1998), 2-cyanopyrrolidides and 4-cyanopyrrolidides as disclosed by Ashworth et al., *Bioorg. & Med. Chem. Lett.*, 6(22):1163-1166 and 2745-2748 (1996) employing dosages as set out in the above references.

The meglitinide which may optionally be employed in combination with the compound of Formula I of the invention may be repaglinide, nateglinide (Novartis) or KAD1229 (mitiglinide) (PF/Kissei), with repaglinide being preferred.

The compound of Formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of Formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of Formula I may be AJ9677 (rafabegron) (Takeda/Dainippon), L750355 (benzenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of Formula I may be orlistat or ATL-962 (Alizyme), with orlistat being preferred.

The serotonin (and dopamine) reuptake inhibitor which may be optionally employed in combination with a compound of Formula I may be sibutramine, topiramate (Johnson & Johnson) or axokine (Regeneron), with sibutramine and topiramate being preferred.

The thyroid receptor agonist which may be optionally employed in combination with a compound of Formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may optionally be employed in combination with a compound of Formula I may be dexamphetamine, phentermine, phenylpropanolamine or mazindol, with dexamphetamine being preferred.

The various anti-obesity agents described above may be employed in the same dosage form with the compound of Formula I or in different dosage forms, in dosages and regimens as generally known in the art or in the PDR.

The antihypertensive agents which may be employed in combination with the compound of Formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al. mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in *Clin. Exp. Pharmacol. Physiol.*, 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxy-carbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in *Eur. Therap. Res.*, 39:671 (1986); 40:543 (1986); ramipril (Hoechsst) disclosed in European Patent No. 79-022 and *Curr. Ther. Res.*, 40:74 (1986); Ru 44570 (Hoechst) disclosed in *Arzneimittelforschung*, 34:1254 (1985), cilazapril (Hoffman-LaRoche) disclosed in *J. Cardiovasc. Pharmacol.*, 9:39 (1987); R 31-2201 (Hoffman-LaRoche) disclosed in *FEBS Lett.*, 165:201 (1984); lisinopril (Merck), indalapril (delapril) disclosed in U.S. Pat. No. 4,385,051; indolapril (Schering) disclosed in *J. Cardiovasc. Pharmacol.*, 5:643, 655 (1983); spirapril (Schering) disclosed in *Acta. Pharmacol. Toxicol.*, 59 (Suppl. 5):173 (1986); perindopril (Servier) disclosed in *Eur. J. Clin. Pharmacol.*, 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in *Pharmacologist*, 26:243, 266 (1984), WY-44221 (Wyeth) disclosed in *J. Med. Chem.*, 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, and 5,525,723, European Patent Applications 0599444, 0481522, 0599444, 0595610, 0534363A2, 534396 and 534492, and 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of Formula I include hydrochlorothiazide, torasemide, furosemide, spironolactono, and indapamide.

Antiplatelet agents which may be employed in combination with compounds of Formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of Formula I of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 0.5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of Formula I of the invention are glucocorticoid receptor modulators as shown either by their ability to bind glucocorticoid receptors in GR binding assays, or by their ability to inhibit AP-1 activity as indicated in cellular transrepressional assays, and cause none to minimal transactivation as indicated in cellular transcriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity ($EC_{50}$ less than 15 µM).

Identical and/or similar assays are described in U.S. application Ser. No. 10/621,807, filed Jul. 17, 2003 which is incorporated in its entirety herein by reference.

GR Binding Assays

Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e., Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e., Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 micro-Molar.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e., are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e., a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g., PMA, lipopolysaccharide, TNF-α, etc) which will induce transcription mediated by AP-1 or NF-κB.

Additionally, AR mediated transrepression may be measured by the assay described in Palvimo, J. J. et al., *J. Biol. Chem.*, 271(39):24151-24156 (Sep. 27, 1996), and PR mediated transrepression may be measured by the assay described in Kalkhoven, E. et al., *J. Biol. Chem.*, 271(11):6217-6224 (Mar. 15, 1996).

Examples of compounds of the present invention prepared by methods described in the general schemes are given in the preparations and examples section set out hereinafter. Example compounds are typically prepared as racemic mixtures. Preparation of Homochiral Examples May be Carried Out by Techniques Known to One skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

ABBREVIATIONS

The following abbreviations are employed in the following Preparations and Examples:
Ph=phenyl
Bn=benzyl
t-Bu=tertiary butyl
Me=methyl
Et=ethyl
ACN=acetonitrile
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-Pr$_2$NEt=diisopropylethylamine
Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride
DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
rt or RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents
Solvent A=10% MeOH-90% H$_2$O-0.1% TFA
Solvent B=90% MeOH-10% H$_2$O-0.1% TFA; or
Solvent A=H$_2$O containing 0.1% TFA
Solvent B=ACN containing 0.1% TFA
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point Methods of Synthesis The compounds of the present invention may be synthesized by many methods available to those skilled in the art of organic chemistry. General synthetic schemes, in accordance with the present invention, for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

Scheme 1 outlines one of the general syntheses for a series of 4,5-di-substituted dihydro-cyclopenta[b]thiophene carboxamides, compound of formula (I). Knoevenagel reaction of β-ketoester 1 with an aldehyde (R$_8$—CHO), using piperidine and acetic acid as catalysts, gives ester 2. Nazarov cyclization of 2 is accomplished with AlCl$_3$ in nitroethane at elevated temperature, to give ethyl 1-oxo-2,3-dihydro-1H-indene-2-carboxylate 3. Alkylation of ketoester 3 can be effected with mild bases such as K$_2$CO$_3$ and alkylating agents R$_7$-LG, where the leaving group (LG) is a chloride, bromide, iodide or sulfonate. Reduction of the ketone carbonyl can be achieved using triethylsilane in the presence of boron trifluoride etherate, to give 5. Saponification of the hindered ester 5 can be sluggish under the standard NaOH/MeOH/H$_2$O at reflux conditions. Addition of DMSO to this mixture usually accelerates the reaction. Coupling of the acid product 6 with amine 7 by one of the many methods of amidation (such as treating 6 with 1-[3-(dimethylamino)propyl]-3-ethylcarbodiimide hydrochloride (EDC), 1-hydroxy-7-azabenzotriazole, triethylamine and amine 7 in a suitable solvent such as acetonitrile) affords compound of formula (I) of the invention.

Scheme 1

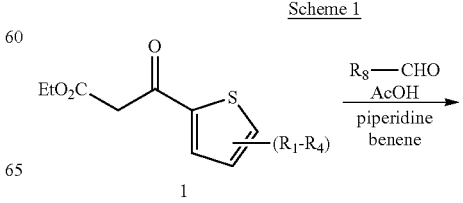

37
-continued

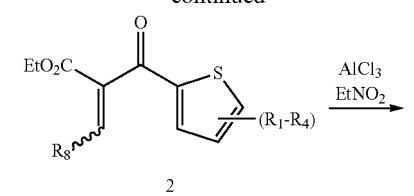

2

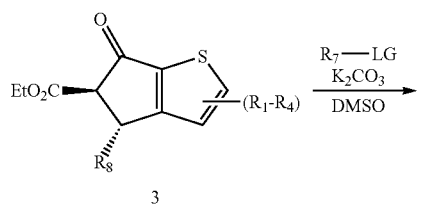

3

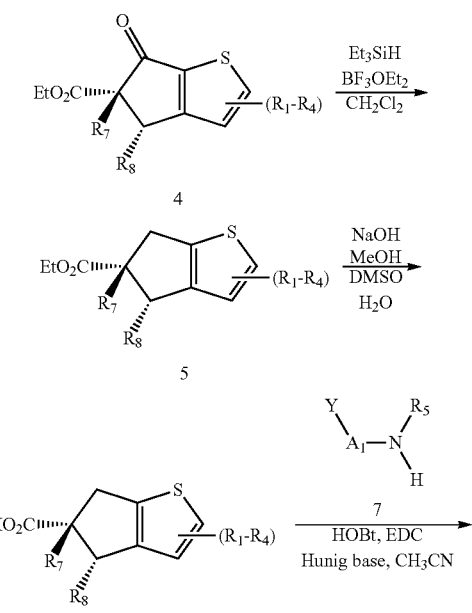

4

5

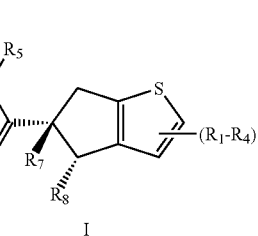

6

I

Scheme 2 outlines a general synthesis for a series of 4,5-di-substituted dihydro-cyclopenta[b]thiophene carboxamides (Ib), wherein $R_{21}$ is an aryl group. A compound of formula (1a) that contains at least one halogen atom (I, Br and Cl) or OTf (triflate) group located in the thiophene ring undergoes metal (such as palladium) catalyzed coupling reaction with an organometallic compound (such as the organoboron or organostannic compound) using one of the methods well known to those skilled in the art to provide a compound of formula (Ib).

38

Scheme 2

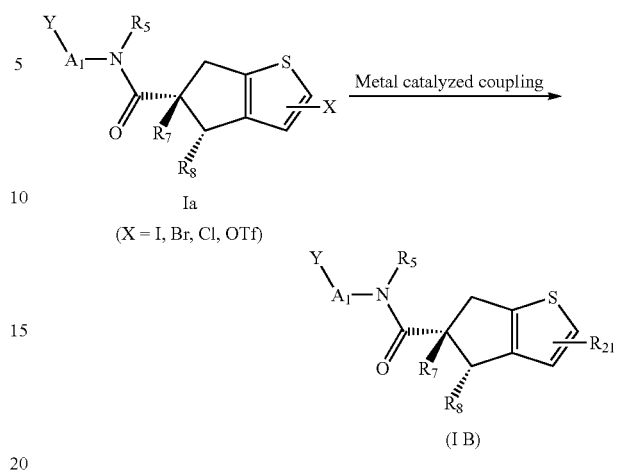

Ia
(X = I, Br, Cl, OTf)

(IB)

EXAMPLES

The following Examples illustrate embodiments of the inventive compounds and starting materials, and are not intended to limit the scope of the claims.

PREPARATIONS

The preparations set out below are for the synthesis of reagents that were not obtained from commercial sources and were employed for the preparation of compounds of Formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20×100, 20×250 or 30×250 millimeter ("mm")). Gradient elution was performed with methanol ("MeOH")/water mixtures in the presence of 0.1% trifluoroacetic acid ("TFA").

Analytical HPLC Methods

Analytical HPLC was performed on Shimadzu SCL10A liquid chromatographs using the following methods: Unless otherwise designated, Method A conditions were used to generated data for compounds appearing throughout the Preparations and Examples.

Method A: Column: YMC Combiscreen ODS-A, 4.6×50 mm, Mobile phase: 10-90% aq $CH_3OH$/0.2% $H_3PO_4$, 4.0 min. gradient with 1.0 min. hold, Flow rate: 4 ml/min, 220 nm detection wavelength.

Method B: Column: XETRRA C-18 4.6×50 mm. Mobile Phase: 10-90% aq CH3OH/0.2% H3PO4, 4.0 min. gradient with 1 in. hold, Flow rate: 4.0 mL/min. 220 nm detection wavelength.

Method C: Column: Phenomenex Synergi C-18 4.6×50 mm, Mobile phase: 10-90% aq CH3OH/0.2% H3PO4, 4.0 min. gradient with 1 min. hold, Flow rate: 4.0 mL/min, 220 nm detection wavelength.

Method D: Column: Shimadzu VP-ODS; C-18 Ballistic 4.6×50 mm. Mobile phase: 10-90% aq CH3OH/0.2%

Preparation 1

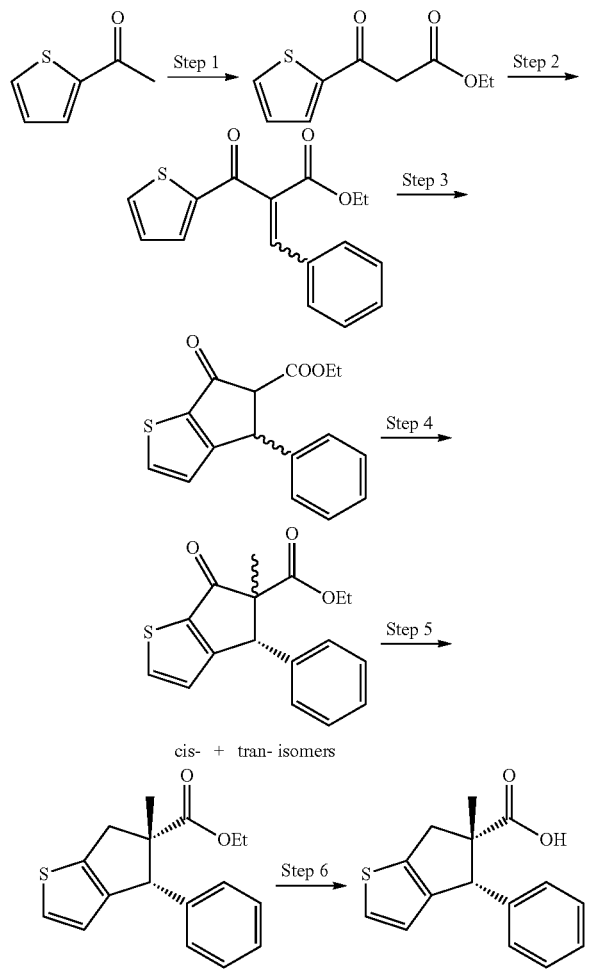

Step 1

To a solution of 1-(thiophen-2-yl)ethanone (2.944 g, 23.3 mmol) and Diethyl carbonate (70 mL) at 0° C. was added sodium hydride (1.86 g, 46.6 mmol). The resulting off-white slurry solution was gradually warmed to 71° C., and stirred for 1.5 hour. The reaction mixture was poured into ice-HOAc—H₂O, and extracted with ethyl acetate. The organic phase was washed (brine), dried (MgSO₄) and concentrated to give a brown liquid. The crude product was purified via flash chromatography (silica gel cartridge with eluent of 0-3% ethyl acetate/hexane) to afford ethyl 3-oxo-3-(thiophen-2-yl)propanoate as an amble liquid, 4.193 g (91%). LCMS m/z 388.99, 390.09 (M+23); HPLC: Rt 2.01 min. (4.0 min. gradient, Column: YMC Combiscreen C-18, Method A).

Step 2

A solution of ethyl 3-oxo-3-(thiophen-2-yl)propanoate (4.10 g, 20.7 mmol), benaldehyde (2.32 ml, 22.8 mmol), piperidine (0.205 ml, 2.07 mmol) and acetic acid (0.593 ml, 10.4 mmol) in benzene (80 ml) was heated at 85° C. for 5 hours using a Dean-Stark trap for removal of the water formed. The reaction solution was concentrated. The resulting residue was purified via flash chromatography (silica gel cartridge with eluent of 0-5% ethyl acetate/hexane) to give ethyl 3-phenyl-2-(thiophene-2-carbonyl)acrylate as a white solid (5.563 g, 94% yield). LCMS m/z 309.1 (M+23); HPLC: Rt 3.15 min.

Step 3

A solution of ethyl 3-phenyl-2-(thiophene-2-carbonyl) acrylate (3.118 g, 10.9 mmol) and aluminum trichloride (1.725 g, 13 mmol) in nitroethane (50 ml) was heated at 75° C. for 3 hours. The reaction mixture was poured into 1N HCl-ice solution, and extracted with ethyl acetate. The organic phase was washed with brine, dried (MgSO₄) and concentrated to give a brown oil. The crude product was purified via flash chromatography 9 (silica gel cartridge with eluent of 0-15% ethyl acetate/hexane) to give ethyl 6-oxo-4-phenyl-5,6-dihydro-4H-cyclopenta[b]thiophene-5-carboxylate as am amble liquid, 3.12 g, quantitative yield. HPLC: Rt 2.873, 3.188 min.

Step 4

A slurry suspension of ethyl 6-oxo-4-phenyl-5,6-dihydro-4H-cyclopenta[b]thiophene-5-carboxylate (0.691 g, 2.415 mmol), iodomethane (0.376 ml, 6.04 mmol) and potassium carbonate (1.669 g, 12.08 mmol) in DMSO (10 ml) was stirred at room temperature for 5 hours. The reaction mixture was taken into water and ethyl ether. The organic phase was washed with brine, dried (MgSO₄) and concentrated to give a yellow oil. The crude material was purified via flash chromatography (silica gel cartridge with eluent of 0-10% ethyl acetate/hexane) to collect three fractions. The fast eluting fraction afforded (trans)-ethyl 5-methyl-6-oxo-4-phenyl-5,6-dihydro-4H-cyclopenta[b]thiophene-5-carboxylate as a white solid (69 mg, 9%). HPLC: Rt 3.365 min; LCMS m/z 301.11 (M+1); $^1$H NMR (400 MHz, chloroform-D) δ ppm 7.98 (1H, d, J=4.78 Hz), 7.27-7.37 (3H, m), 6.95-7.04 (3H, m), 5.01 (1H, s), 4.25 (2H, q, J=7.13 Hz), 1.28 (3H, t, J=7.18 Hz), 1.00 (3H, s). The slow eluting fraction afforded (cis)-ethyl 5-methyl-6-oxo-4-phenyl-5,6-dihydro-4H-cyclopenta[b]thiophene-5-carboxylate as a white solid, (469 mg, 65% yield). $^1$H NMR (400 MHz, chloroform-D) δ ppm 7.98 (1H, d, J=4.78 Hz), 7.26-7.31 (3H, m), 7.09 (2H, dd, J=7.18, 2.39 Hz), 6.98 (1H, d, J=4.53 Hz), 4.39 (1H, s), 3.60 (1 H, m), 3.43 (1H, m), 1.72 (3H, s), 0.80 (3H, t, J=7.18 Hz). HPLC: Rt 3.125 min; LCMS m/z 323.01, 301.11 (M+1)]. In addition, a cis/trans mixture (68 mg) was obtained to afford a total yield of 84% for the Step 4 of Preparation 1.

Step 5

A solution of (cis)-ethyl 5-methyl-6-oxo-4-phenyl-5,6-dihydro-4H-cyclopenta[b]thiophene-5-carboxylate (0.337 g, 1.123 mmol), boron trifluoride diethyl etherate (7.15 ml, 50 mmol) and triethylsilane (7.15 ml, 40 mmol) in dichloromethane (8 ml) was stirred at room temperature for 24 hours. The reaction mixture was taken into 1/1 Et2O-hexane and sat'd NaHCO₃ solution. After separation, the organic phase was washed, dried and concentrated to the crude product. The crude product was purified via flash chromatography (silica gel cartridge with eluent of 0-5% ethyl acetate/hexane) to afford (cis)-ethyl 5-methyl-4-phenyl-5,6-dihydro-4H-cyclopenta[b]thiophene-5-carboxylate as a white solid (289 mg, 89.9% yield). $^1$H NMR (400 MHz, chloroform-D) δ ppm 7.13-7.23 (4H, m), 6.93-7.00 (2H, m), 6.63 (1H, d, J=5.04 Hz), 4.07 (1H, d, J=1.26 Hz), 3.86 (1H, d, J=15.86 Hz), 3.59-3.70 (1H, m), 3.49-3.58 (1H, m), 2.74 (1H, d, J=15.86 Hz), 1.62 (3H, s), 0.86 (3H, t, J=7.18 Hz). HPLC: Rt 3 min. LCMS m/z 213.07 (M-COOEt)].

Step 6

A solution of (cis)-ethyl 5-methyl-4-phenyl-5,6-dihydro-4H-cyclopenta[b]thiophene-5-carboxylate (289 mg, 1.01 mmol) and 40% KOH aq. solution (3 ml) in DMSO (1.5 ml)

and MeOH (4.5 ml) was stirred at 74° C. overnight. The reaction solution was concentrated and the residue was dissolved in water. The solution was adjusted to acidic with conc. HCl followed by extraction with ethyl ether. The organic phase was washed, dried (MgSO$_4$) and evaporated to provide the cis-5-methyl-4-phenyl-5,6-dihydro-4H-cyclopenta[b]thiophene-5-carboxylic acid as a white solid (240 mg, 92% yield). $^1$H NMR (400 MHz, chloroform-D) δ ppm 7.14-7.23 (4H, m), 6.98 (2H, dd, J=7.53, 1.76 Hz), 6.64 (1H, d, J=5.02 Hz), 4.11 (1H, s), 3.78 (1H, d, J=15.81 Hz), 2.76 (1H, d, J=15.81 Hz), 1.64 (3H, s). HPLC: Rt 3.49 min. LCMS m/z 259.2 (M+1).

Preparation 2

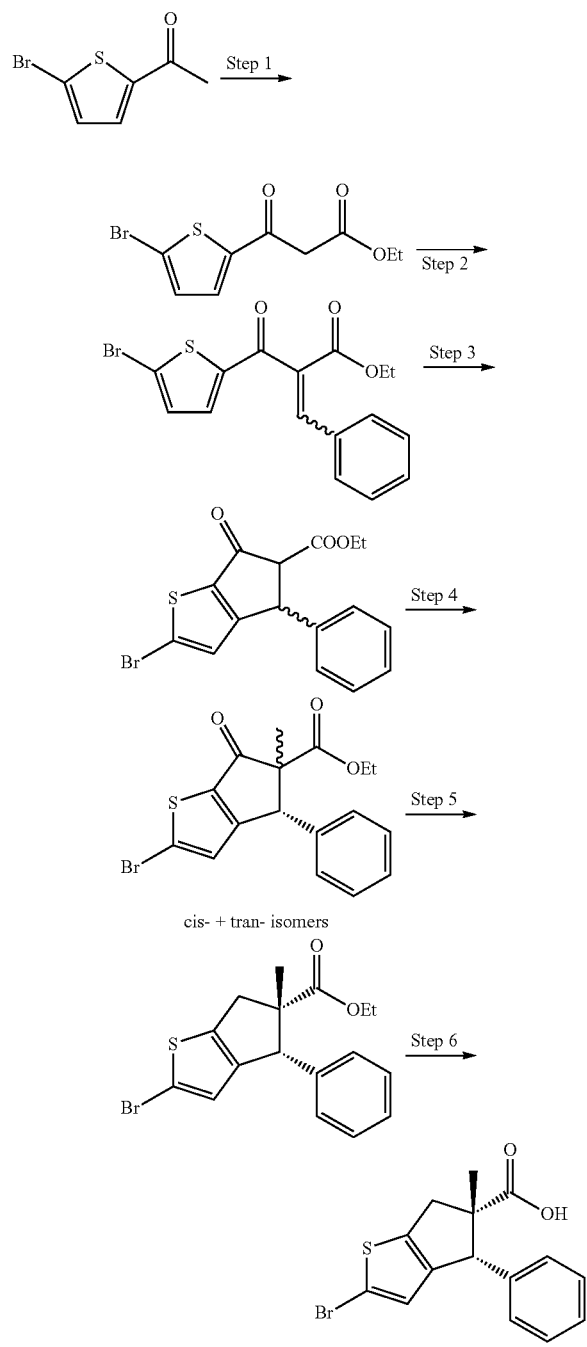

cis- + tran- isomers

Step 1

To a solution of 1-(5-bromothiophen-2-yl)ethanone (4.10 g, 19.99 mmol) and Diethyl carbonate (30 mL, 248 mmol) in THF (40 ml) at room temperature was added sodium hydride (1.679 g, 42.0 mmol). The resulting off-white slurry solution was gradually warmed to 56° C., and became dark brown clear solution. The reaction mixture was heated at 56° C. for 1.5 hour. The reaction mixture was poured into ice-HOAc—H$_2$O, and extracted with ethyl acetate. The organic phase was washed (brine), dried (MgSO$_4$) and concentrated to give a brown liquid. The crude product was purified via flash chromatography (silica gel cartridge with eluent of 0-5% ethyl acetate/hexane) to afford ethyl 3-(5-bromothiophen-2-yl)-3-oxopropanoate as an amble liquid, 4.713 g (85%). HPLC: Rt 2.856 min.

Step 2

A solution of ethyl 3-(5-bromothiophen-2-yl)-3-oxopropanoate (3.73 g, 13.46 mmol), benaldehyde (1.501 ml, 14.81 mmol), piperidine (0.133 ml, 1.346 mmol) and acetic acid (0.389 ml, 6.8 mmol) in benzene (50 ml) was heated at 85° C. for 5 h using a Dean-Stark trap for removal of the water formed. The reaction solution was concentrated. The resulting residue was purified via flash chromatography (silica gel cartridge with eluent of 0-5% ethyl acetate/hexane) to give ethyl 2-(5-bromothiophene-2-carbonyl)-3-phenylacrylate as a light amble viscous oil (4.25 g). LCMS m/z 388.99, 390.09 (M+23); HPLC: Rt 3.701 min.

Step 3

A solution of ethyl 2-(5-bromothiophene-2-carbonyl)-3-phenylacrylate (1.3 g, 3.56 mmol) and aluminum trichloride (0.563 g, 4.27 mmol) in nitroethane (20 ml) was heated at 83° C. for 2.75 hours. The reaction mixture was poured into 1N HCl-ice solution, and extracted with ethyl acetate. The organic phase was washed with brine, dried (MgSO$_4$) and concentrated to give a brown oil. The crude product was purified by silica gel flash chromatography using 0-5% ethyl acetate in hexanes to give ethyl 2-bromo-6-oxo-4-phenyl-5,6-dihydro-4H-cyclopenta[b]thiophene-5-carboxylate as a viscous foam (1.024 g, 78.8% yield). LCMS m/z 366, 368 (M+1); 388.9, 386.9 (M+23); HPLC: Rt 3.438, 3.718 min.

Step 4

A slurry suspension of ethyl 2-bromo-6-oxo-4-phenyl-5,6-dihydro-4H-cyclopenta[b]thiophene-5-carboxylate (1.024 g, 2.804 mmol), iodomethane (0.437 ml, 7.01 mmol) and potassium carbonate (1.938 g, 14.02 mmol) in DMSO (12 ml) was stirred at room temperature for 5 hours. The reaction mixture was taken into water and ethyl ether. The organic phase was washed with brine, dried (MgSO$_4$) and concentrated to give a yellow oil. The crude material was purified via by flash chromatography (silica gel cartridge with eluent of 0-10% ethyl acetate/hexane) to give (cis)-ethyl 2-bromo-5-methyl-6-oxo-4-phenyl-5,6-dihydro-4H-cyclopenta[b]thiophene-5-carboxylate as a yellow viscous oil, (693.7 mg, 65.3% yield) [HPLC: Rt 3.655 min; LCMS m/z 381, 379] and (trans)-ethyl 2-bromo-5-methyl-6-oxo-4-phenyl-5,6-dihydro-4H-cyclopenta[b]thiophene-5-carboxylate as a white solid (120.8 mg, 11.4%). HPLC: Rt 3.828 min; LCMS m/z 380.97, 378.97.

Step 5

A solution of (cis)-ethyl 2-bromo-5-methyl-6-oxo-4-phenyl-5,6-dihydro-4H-cyclopenta[b]thiophene-5-carboxylate (0.36 g, 0.949 mmol), boron trifluoride diethyl etherate (5.96 ml, 47.5 mmol) and triethylsilane (6.06 ml, 38.0 mmol) in dichloromethane (5 ml) was stirred at room temperature for 120 hours. The reaction solution was treated with DMSO (5.39 ml, 76 mmol) at 0° C. and stirred for 10 min. until no more bubble formed. The reaction mixture was taken into 1/1

Et2O-hexane and sat'd NaHCO3 solution. After separation, the organic phase was washed, dried and concentrated to the crude product. The crude product was purified via flash chromatography (silica gel cartridge with eluent of 0-5% ethyl acetate/hexane) to afford (cis)-ethyl 2-bromo-5-methyl-4-phenyl-5,6-dihydro-4H-cyclopenta[b]thiophene-5-carboxylate as a clear oil, 235 mg (67.8% yield, 79% based on the recovered starting material). $^1$H NMR (400 MHz, MeOD) δ ppm 7.23-7.45 (3H, m), 7.19 (1H, s), 7.11 (2H, dd, J=7.43, 1.64 Hz), 4.56 (1H, s), 3.56 (1H, m), 3.43 (1H, m), 1.65 (3H, s), 0.82 (3H, t, J=7.18 Hz). HPLC: Rt 4.148 min. LCMS m/z 389,387 (M+23), and un-reacted (cis)-ethyl 2-bromo-5-methyl-6-oxo-4-phenyl-5,6-dihydro-4H-cyclopenta[b]thiophene-5-carboxylate (50 mg).

Step 6

A solution of (cis)-ethyl 2-bromo-5-methyl-4-phenyl-5,6-dihydro-4H-cyclopenta[b]thiophene-5-carboxylate (235 mg, 0.643 mmol) and 40% KOH aq. solution (3.5 ml) in DMSO (1.5 ml) and MeOH (4.5 ml) was stirred at 74.5° C. overnight. The reaction solution was concentrated and the residue was dissolved in water. The solution was adjusted to acidic with conc. HCl followed by extraction with ethyl ether. The organic phase was washed, dried (MgSO4) and evaporated to give an off-white viscous solid. The crude product was purified via the flash chromatography (silica gel cartridge with eluent of 0-10% ethyl acetate/hexane) to give the cis-2-bromo-5-methyl-4-phenyl-5,6-dihydro-4H-cyclopenta[b]thiophene-5-carboxylic acid as a white solid (195 mg, 90% yield). $^1$H NMR (400 MHz, MeOD) δ ppm 7.11-7.23 (3H, m), 6.96-7.03 (2H, m), 6.64 (1H, s), 4.08 (1H, s), 3.74 (1H, d, J=16.12 Hz), 2.71 (1H, d, J=15.86 Hz), 1.60 (3H, s); HPLC: Rt 3.853 min. LCMS m/z 338.97, 336.97 (M+1).

Preparation 3

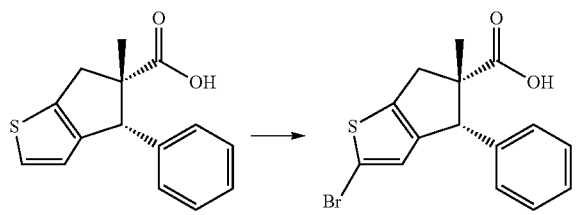

To a solution of the acid of Preparation (1), (cis)-5-methyl-4-phenyl-5,6-dihydro-4H-cyclopenta[b]thiophene-5-carboxylic acid (240 mg, 0.929 mmol), and sodium acetate (114 mg, 1.394 mmol) in AcOH (4.65 ml) was added bromine (0.048 ml, 1 equiv.) slowly at room temperature. The reaction solution was stirred for 6 hours. HPLC indicated 66% starting material was converted to the product. Additional 0.3 equiv. Br2 was added. After one hour, the reaction was completed. The reaction mixture was poured into 10% solution of sodium thiosulfate (Na2S2O3) and extracted with diethyl ether. After separation, the organic layer was washed with water, 10% NH4OH, brine, dried (MgSO4) and concentrated to give (cis)-2-bromo-5-methyl-4-phenyl-5,6-dihydro-4H-cyclopenta[b]thiophene-5-carboxylic acid as a white solid (289 mg, 92% yield). $^1$H NMR (400 MHz, MeOD) δ ppm 7.07-7.55 (3H, m), 6.99 (2H, dd, J=8.18, 1.38 Hz), 6.64 (1H, s), 4.08 (1H, d, J=1.51 Hz), 3.74 (1H, d, J=16.12 Hz), 2.71 (1H, d, J=15.86 Hz), 1.60 (3H, s). HPLC: Rt 3.853 min. LCMS ES$^-$ m/z 335, 337.0 (M−1).

Preparation 4

The acid of preparation (3) was resolved into its corresponding enantiomers, acid of Preparation (4a) and (4b) using chiral supercritical fluid chromatography (SFC) with the following conditions.

Chiral-SFS Prep. Conditions:

Preparative Column: Chiralcel OJ-H (3×25 cm, 5 μm)

BPR pressure: 100 bars

Temperature: 40° C.

Flow rate: 70 mL/min

Mobile Phase: CO2/MeOH (90/10)

Detector Wavelength: 210 nm

Separation Program: Sequence injection

Analytical HPLC (Column: OJ-H 250×4.6 mm 5 micron, Mobile phase: CO2/MeOH, Flowrate: 90/10 2 ml/min, BPR pressure: 00 Bar temperature: 40° C. Detection: UV220 nm) Retention times: Enantiomer A (4a): 5.27 min (ee>99.9%); Enantiomer B (4b): 7.25 min (ee 98.8%).

In general, if the absolute stereochemistry of the two enantiomers are not yet defined. Isomer A designates the fast eluting enantiomer, and Isomer B the slow eluting enantiomer.

A sample of the slow-eluting isomer (4b) co-crystallized with R-(+)-β-methyl phenethyl amine in MeCN.EtOH. An X-ray crystal structure determination of the crystalline material thus obtained has proved (4b) to be of (4R, 5R) configuration. The configuration of (4a), the antipode of (4b), thus was assigned as (4S, 5S).

| Preparation | Structure | HPLC Rt minute | LC MS [m/z (M + H)] |
|---|---|---|---|
| 4a | Enantiomer A (4S,5S) | 3.873 | 337.1, 335.1 |
| 4b | Enantiomer B (4R,5R) | 3.876 | 337.1, 335.1 |

Example 1

(+/−)-2-Bromo-5-methyl-4-phenyl-N-(1,3,4-thiadiazol-2-yl)-5,6-dihydro-4H-cyclopenta[b]thiophene-5-carboxamide

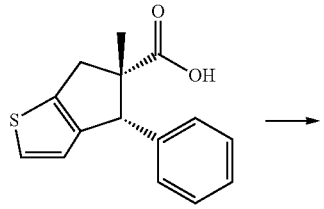

To a solution of the acid of Preparation 1 (190 mg, 0.563 mmol) in CH$_3$CN (6 mL) were added 1-[3-(dimethylamino)propyl]-3-ethylcarbodiimide hydrochloride (EDC) (162 mg, 0.845 mmol) and 1-hydroxy-7-benzotriazole (HOBt) (129 mg, 0.845 mmol). After stirring for 5 minutes, to the solution were added 2-Amino-1,3,4-thiadiazole (171 mg, 1.690 mmol) and N,N-diisopropylethylamine (0.442 ml, 2.54 mmol). The reaction was heated at 75° C. for 15 hours. The reaction mixture was filtered, concentrated and purified via the flash chromatography (silica gel cartridge with eluent of 0-40% ethyl acetate/hexane) to give the title compound of Example 1 as a white solid (119 mg, 51% yield). $^1$H NMR (400 MHz, CDCl$_3$) δ ppm 11.50 (1H, s), 8.71 (1H, s), 7.01-7.14 (3H, m), 6.96 (2H, d, J=7.30 Hz), 6.71 (1H, s), 4.79 (1H, s), 4.05 (1H, d, J=16.12 Hz), 2.83 (1H, d, J=15.86 Hz), 1.81 (3 H, s). LC/MS (m/z) 418.1, 420.0; HPLC Rt: 3.731 min.

Examples 2 and 3

(4S,5S)-2-Bromo-5-methyl-4-phenyl-N-(1,3,4-thiadiazol-2-yl)-5,6-dihydro-4H-cyclopenta[b]thiophene-5-carboxamide and (4R,5R)-2-Bromo-5-methyl-4-phenyl-N-(1,3,4-thiadiazol-2-yl)-5,6-dihydro-4H-cyclopenta[b]thiophene-5-carboxamide In a similar manner to Example 1, Examples 2 and 3 were prepared via the amidation reactions of acids of Preparations (4a) and (4b) with 2-amino-1,3,4-thiadiazole respectively.

| Example | Structure | HPLC Rt minute | LC MS [m/z (M + H)] | $^1$H NMR δ ppm |
|---------|-----------|----------------|---------------------|-----------------|
| 2 | 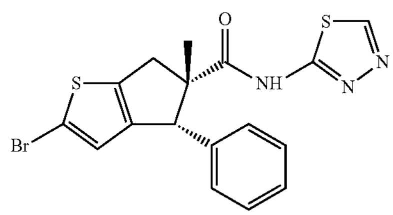 | 3.715 | 422, 420 | (400 MHz, CDCl$_3$): 11.34 (1 H, s), 8.71 (1 H, s), 7.01-7.13 (3 H, m), 6.93-7.00 (2 H, m), 6.71 (1 H, s), 4.76 (1 H, s), 4.03 (1 H, d, J = 15.36 Hz), 2.84 (1 H, d, J = 16.12 Hz), 1.81 (3 H, s) |
| 3 | 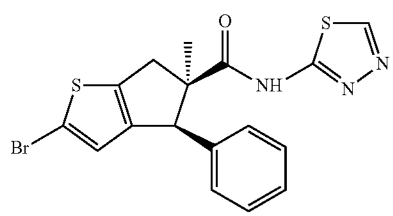 | 3.700 | 422, 420 | (400 MHz, CDCl$_3$): 11.34 (1 H, s), 8.71 (1 H, s), 7.01-7.13 (3 H, m), 6.93-7.00 (2 H, m), 6.71 (1 H, s), 4.76 (1 H, s), 4.03 (1 H, d, J = 15.36 Hz), 2.84 (1 H, d, J = 16.12 Hz), 1.81 (3 H, s) |

-continued

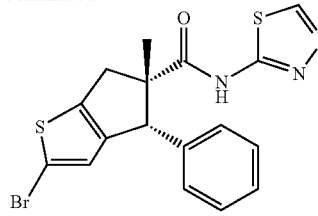

Example 4

(+/−)-Cis-2-(4-(ethylmethyl)carbamoyl)phenyl)-5-methyl-4-phenyl-N-(1,3,4-thiadiazol-2-yl)-5,6-dihydro-4H-cyclopenta[b]thiophene-5-carboxamide

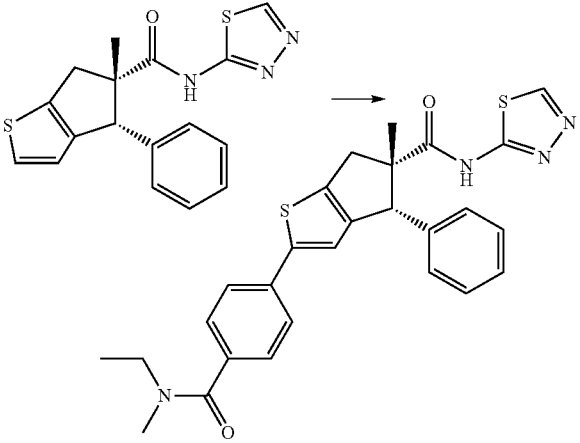

A solution of the title compound of Example 1, cis-2-bromo-5-methyl-4-phenyl-N-(1,3,4-thiadiazol-2-yl)-5,6-dihydro-4H-cyclopenta[b]thiophene-5-carboxamide (35 mg, 0.083 mmol), 4-(ethyl(methyl)carbamoyl)phenylboronic acid (34.5 mg, 0.167 mmol) and potassium phosphate (0.167 ml, 0.333 mmol) in DMF (1.8 ml) was degassed with nitrogen for 15 min. To this solution was added tetrakis (triphenyl phosphine)palladium(0) (9.62 mg, 8.33 μmol). The reaction mixture was degassed for additional 5 min, then sealed and heated in a heating block (OptiChem Digital Hotplate Stirrer) at 100° C. for 30 min. The reaction mixture was cooled, filtered, and diluted with ethyl acetate. The organic solution was washed, dried and concentrated. The crude product was purified by prep HPLC [Column: YMC 20×100; Mobile phase: B in A: 60%-100% (A: 10% MeOH in $H_2O$ with 0.1% TFA, B: 90% MeOH in $H_2O$ with 0.1% TFA); gradient time: 12 min.] to give the title compound of Example 3 as a white solid (14 mg, 34% yield). $^1$H NMR (400 MHz, $CDCl_3$) δ ppm 10.93 (1H, s), 8.70 (1H, s), 7.48-7.68 (2H, m), 7.38 (2H, d, J=8.06 Hz), 7.01-7.17 (5H, m), 6.99 (1H, s), 4.71 (1H, s), 4.06 (1H, d, J=16.62 Hz), 3.58 (1H, s), 3.31 (1H, s), 3.00-3.14 (3H, m), 2.95 (1H, d, J=16.37 Hz), 1.85 (3H, s). HPLC 3.56 min; LCMS m/z 503.10 (M+1).

Examples 5 to 11

In a similar manner to Example 4, Examples 5 to 11 were prepared via the Suzuki coupling reaction of the title compound of Example 1 and the corresponding aryl boronic acids. (All compounds are racemic unless noted.)

| Example | R = | HPLC Rt minute | LC MS [m/z (M + H)] | $^1$H NMR (δ ppm) |
|---|---|---|---|---|
| 5 | 4-(N-methyl-N-methylcarbamoyl)phenyl | 3.433 | 489.1 | (400 MHz, MeOD): 8.88 (1 H, s), 7.64 (2 H, d, J = 8.31 Hz), 7.41 (2 H, d, J = 8.31 Hz), 6.77-7.18 (6 H, m), 4.32 (1 H, s), 4.12 (1 H, d, J = 16.37 Hz), 3.09 (3 H, s), 3.02 (3 H, s), 2.85 (1 H, d, J = 16.37 Hz), 2.85 (1 H, d, J = 16.37 Hz), 1.79 (3 H, s) |
| 6 | 2-chloro-4-(N,N-dimethylcarbamoyl)phenyl | 3.568 | 523.0 | (400 MHz, $CDCl_3$): 11.44 (1 H, s), 8.73 (1 H, s), 7.54 (1 H, s), 7.41-7.49 (1 H, m), 7.26 (1 H, d, J = 7.55 Hz), 6.90-7.14 (6 H, m), 4.81 (1 H, s), 4.13 (1 H, d, J = 16.37 Hz), 3.13 (3 H, s), 2.92 (1 H, d, J = 16.62 Hz), 2.88 (3 H, s), 1.85 (3 H, s) |
| 7 | 4-(morpholine-4-carbonyl)phenyl | 3.390 | 531.1 | (400 MHz, MeOD) 8.87 (1 H, s), 7.65 (2 H, d, J = 8.31 Hz), 7.41 (2 H, d, J = 8.56 Hz), 6.81-7.15 (5 H, m), 4.31 (1 H, s), 4.11 (1 H, d, J = 16.37 Hz), 3.39-3.85 (8 H, m), 2.85 (1 H, d, J = 16.37 Hz), 1.79 (3 H, s) |
| 8 | 4-(pyrrolidine-1-carbonyl)phenyl | 3.610 | 515.1 | (400 MHz, $CDCl_3$): 11.00 (1 H, s), 8.72 (1 H, s), 7.38-7.73 (2 H, m), 6.86-7.16 (6 H, m), 4.75 (1 H, s), 4.08 (1 H, d, J = 16.37 Hz), 3.64 (2 H, t, J = 6.67 Hz), 3.45 (2 H, t, J = 6.42 Hz), 2.95 (1 H, d, J = 16.37 Hz), 1.87-2.09 (4 H, m), 1.84 (3 H, s) |
| 9 | 2-fluoro-4-(N,N-dimethylcarbamoyl)phenyl | 3.473 | 507.1 | (400 MHz, MeOD) 8.87 (1 H, s), 7.47 (1 H, dd, J = 7.93, 1.64 Hz), 7.29-7.43 (2 H, m), 7.11 (1 H, s), 6.97-7.09 (5 H, m), 4.32 (1 H, s), 4.12 (1 H, d, J = 16.37 Hz), 3.10 (3 H, s), 2.96 (3 H, d, J = 1.01 Hz), 2.86 (1 H, d, J = 16.62 Hz), 1.79 (3 H, s) |

-continued

| Example | R = | HPLC Rt minute | LC MS [m/z (M + H)] | ¹H NMR (δ ppm) |
|---|---|---|---|---|
| 10 | N-ethyl-N-methyl-2-fluorobenzamide group | 3.621 | 521.1 | (400 MHz, MeOD) 8.87 (1 H, s), 7.43-7.50 (1 H, m), 7.40 (1 H, dd, J = 10.95, 1.89 Hz), 7.33 (1 H, t, J = 7.18 Hz), 6.96-7.14 (6 H, m), 4.32 (1 H, s), 4.12 (1 H, d, J = 16.62 Hz), 3.58 (1 H, d, J = 7.05 Hz), 3.25-3.29 (1 H, m), 3.07 (1.5 H, s), 2.94 (1.5 H, s), 2.86 (1 H, d, J = 16.62 Hz), 1.79 (3 H, s), 1.22 (1.5 H, t, J = 7.18 Hz), 1.12 (1.5 H, t, J = 7.18 Hz) |
| 11 | N-ethyl-N-methyl-2-chlorobenzamide group | 3.711 | 537.0 | (400 MHz, MeOD) 8.87 (1 H, s), 7.63-7.70 (1 H, m), 7.53-7.62 (1 H, m), 7.29 (1 H, dd, J = 7.93, 5.41 Hz), 6.91-7.15 (6 H, m), 4.32 (1 H, s), 4.12 (1 H, d, J = 16.37 Hz), 3.6-3.35 (m, 1H), 3.22 (1 H, m), 3.08 (1.5 H, s), 2.87 (1.5 H, s), 2.86 (1 H, d, J = 16.37), 1.79 (3 H, s), 1.24 (1.5 H, t, J = 7.18 Hz), 1.11 (1.5 H, t, J = 7.18 Hz) |

Examples 12 to 17

In a similar manner to Example 4, Examples 12 to 17 were prepared via the Suzuki coupling reaction of the title compound of Example 2 and the corresponding aryl boronic acids. (All compounds have the (4S, 5S) configuration.)

| Example | R = | HPLC Rt minute | LC MS [m/z (M + H)] | ¹H NMR (δ ppm) |
|---|---|---|---|---|
| 12 | N,N-dimethylbenzamide group | 3.386 | 489.2 | (400 MHz, MeOD): 8.88 (1 H, s), 7.64 (2 H, d, J = 8.31 Hz), 7.41 (2 H, d, J = 8.31 Hz), 6.77-7.18 (6 H, m), 4.32 (1 H, s), 4.12 (1 H, d, J =16.37 Hz), 3.09 (3 H, s), 3.02 (3 H, s), 2.85 (1 H, d, J = 16.37 Hz), 2.85 (1 H, d, J = 16.37 Hz), 1.79 (3 H, s) |

-continued

| Example | R = | HPLC Rt minute | LC MS [m/z (M + H)] | ¹H NMR (δ ppm) |
|---|---|---|---|---|
| 13 | (morpholine benzoyl) | 3.338 | 531.2 | (400 MHz, MeOD) 8.87 (1 H, s), 7.65 (2 H, d, J = 8.31 Hz), 7.41 (2 H, d, J = 8.31 Hz), 6.81-7.20 (6 H, m), 5.48 (1 H, s), 4.32 (1 H, s), 4.11 (1 H, d, J = 16.37 Hz), 3.40-3.87 (8 H, m), 2.85 (1 H, d, J = 16.37 Hz), 1.79 (3 H, s) |
| 14 | (N,N-dimethyl-2-chlorobenzamide) | 3.531 | 523.0 | (400 MHz, CDCl₃): 11.44 (1 H, s), 8.73 (1 H, s), 7.54 (1 H, s), 7.41-7.49 (1 H, m), 7.26 (1 H, d, J = 7.55 Hz), 6.90-7.14 (6 H, m), 4.81 (1 H, s), 4.13 (1 H, d, J = 16.37 Hz), 3.13 (3 H, s), 2.92 (1 H, d, J = 16.62 Hz), 2.88 (3 H, s), 1.85 (3 H, s) |
| 15 | (N-ethyl-N-methylbenzamide) | 3.526 | 503.2 | (400 MHz, CDCl₃): 10.93 (1 H, s), 8.70 (1 H, s), 7.48-7.68 (2 H, m), 7.38 (2 H, d, J = 8.06 Hz), 7.01-7.17 (5 H, m), 6.99 (1 H, s), 4.71 (1 H, s), 4.06 (1 H, d, J = 16.62 Hz), 3.58 (1 H, s), 3.31 (1 H, s), 3.00-3.14 (3 H, m), 2.95 (1 H, d, J = 16.37 Hz), 1.85 (3 H, s) |
| 16 | (pyrrolidine benzoyl) | 3.581 | 515.2 | (400 MHz, CDCl₃): 11.00 (1 H, s), 8.72 (1 H, s), 7.38-7.73 (2 H, m), 6.86-7.16 (6 H, m), 4.75 (1 H, s), 4.08 (1 H, d, J = 16.37 Hz), 3.64 (2 H, t, J = 6.67 Hz), 3.45 (2 H, t, J = 6.42 Hz), 2.95 (1 H, d, J = 16.37 Hz), 1.87-2.09 (4 H, m), 1.84 (3 H, s) |

Examples 18 and 19

In a similar manner to Example 4, Examples 18 and 19 were prepared via the Suzuki coupling reaction of the title compound of Example 3 and the corresponding aryl boronic acids. (All compounds have the (4R, 5R) configuration.)

| Example | R = | HPLC Rt minute | LC MS [m/z (M + H)] | 1H NMR (δ ppm) |
|---|---|---|---|---|
| 18 | (morpholine-carbonyl-phenyl) | 3.36 | 531.2 | (400 MHz, MeOD) 8.87 (1 H, s), 7.65 (2 H, d, J = 8.31 Hz), 7.41 (2 H, d, J = 8.56 Hz), 6.81-7.15 (5 H, m), 4.31 (1 H, s), 4.11 (1 H, d, J = 16.37 Hz), 3.39-3.85 (8 H, m), 2.85 (1 H, d, J = 16.37 Hz), 1.79 (3 H, s) |
| 19 | (N,N-dimethylcarbamoyl-phenyl) | 3.37 | 489.2 | (400 MHz, MeOD) 8.87 (1 H, s), 7.64 (2 H, d, J = 8.31 Hz), 7.41 (2 H, d, J = 8.31 Hz), 6.70-7.19 (6 H, m), 4.32 (1 H, s), 4.11 (1 H, d, J = 16.62 Hz), 3.09 (3 H, s), 3.02 (3 H, s), 2.85 (1 H, d, J = 16.37 Hz), 1.79 (3 H, s) |

Example 20

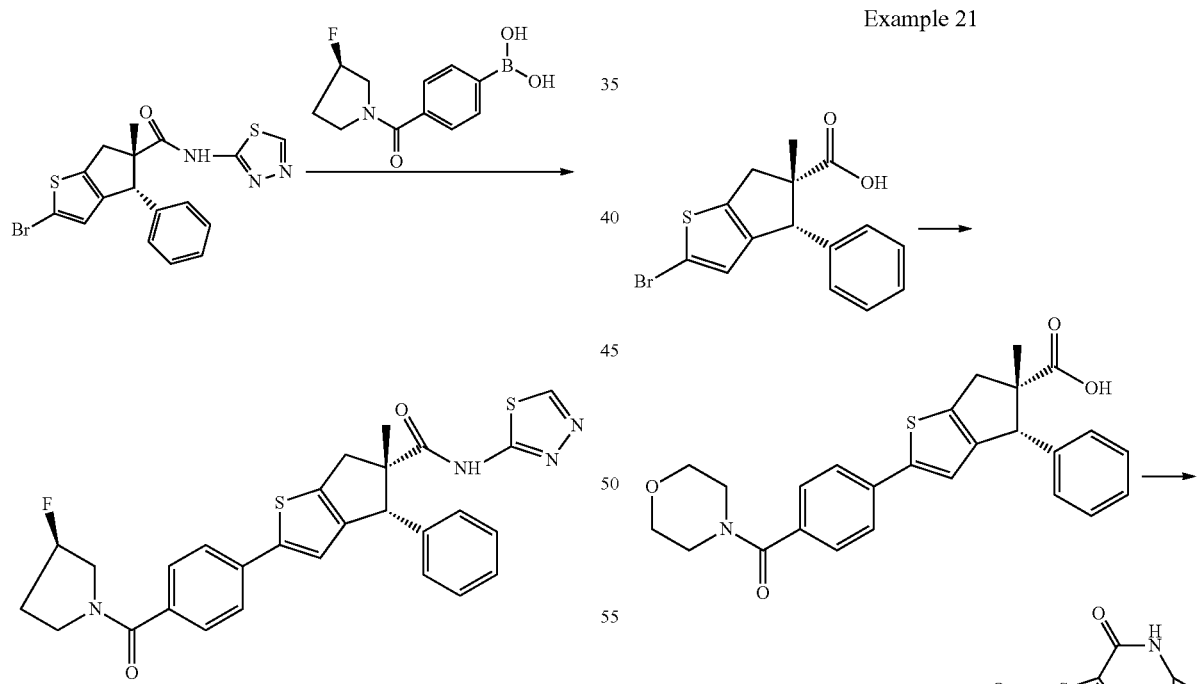

In a similar manner to Example 4, the title compound of Examples 20 was prepared via the Suzuki coupling reaction of the title compound of Example 1 and (R)-4-(3-fluoropyrrolidine-1-carbonyl)phenylboronic acid. 1H NMR (400 MHz, CDCl₃) δ ppm 8.65 (1H, s), 7.54-7.59 (3H, m), 7.50 (1H, t, J=8 Hz), 7.07-7.13 (2H, m), 7.05 (1H, d, J=6.78 Hz), 6.99-7.03 (2H, m), 6.97 (1H, s), 5.27 (1H, t, J=4.8 Hz), 4.46 (1H, s), 4.07 (1H, d, J=16.31 Hz), 3.55-3.97 (4H, m), 2.96 (1H, d, J=16.31 Hz), 2.21-2.42 (1H, m), 1.93-2.10 (1H, m), 1.86 (3H, s); LCMS (m/z) 533.2; HPLC Rt: 3.536 min. (Method A).

Example 21

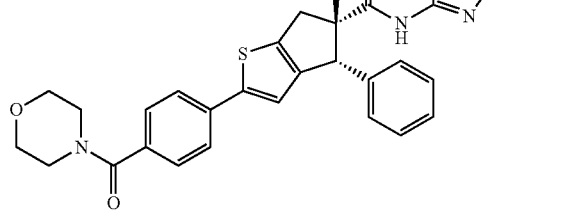

Step 1: (Cis)-5-methyl-2-(4-(morpholine-4-carbonyl) phenyl)-4-phenyl-5,6-dihydro-4H-cyclopenta[b]thiophene-5-carboxylic acid A solution of the acid of Preparation 2, (cis)-2-bromo-5-methyl-4-phenyl-5,6-dihydro-4H-cyclopenta[b]thiophene-5-carboxylic acid (80 mg, 0.237 mmol), 4-(morpholine-4-carbonyl)phenylboronic acid (112 mg, 0.474 mmol) and 2M potassium phosphate (0.593 ml, 1.186 mmol) in DMF (2 ml) was degassed with nitrogen for 15 min. To this solution was added tetrakis (triphenyl phosphine)palladium(0) (27.4 mg, 0.024 mmol). The reaction mixture was degassed for additional 5 min, then sealed and heated in a heating block (OptiChem Digital Hotplate Stirrer) at 110° C. for 50 min. The reaction mixture was cooled, filtered, and was taken into ethyl acetate and water. The organic phase was washed (brine), dried (MgSO4) and concentrated to give the crude (177 mg), which was purified via flash silica gel column eluting with 0-1% MeOH in CHCl$_3$ to give (cis)-5-methyl-2-(4-(morpholine-4-carbonyl)phenyl)-4-phenyl-5,6-dihydro-4H-cyclopenta[b]thiophene-5-carboxylic acid as a white solid, (86 mg, 81% yield). 1H NMR (500 MHz, MeOD) δ ppm 7.64 (2H, d, J=8.25 Hz), 7.40 (2H, d, J=8.25 Hz), 7.20 (2H, t, J=7.15 Hz), 7.15 (1H, d, J=7.15 Hz), 7.05 (3H, m), 4.12 (1H, s), 3.83 (1H, d, J=15.95 Hz), 3.72 (4H, m), 3.63 (2H, m), 3.49 (2H, m), 2.78 (1H, d, J=15.95 Hz), 1.64 (3H, s). LCMS (m/z) 448.1; HPLC Rt: 3.361 min (Method A).

Step 2

A solution of the acid of Step 1 (25 mg, 0.056 mmol), HATU (31.9 mg, 0.084 mmol), 5-amino-N-cyclopropyl-1,3,4-thiadiazole-2-carboxamide (30.9 mg, 0.168 mmol) and DIPEA (0.059 mL, 0.335 mmol) in acetonitrile (2.5 mL) was heated at 70° C. for 15 h. After removal of the solvent, the reaction mixture was taken into DCM and charged to a 12 g silica gel cartridge which was eluted with 0% to 1% MeOH in DCM to give the desired product as an off-white solid (35 mg of 93% purity, 95% yield). It was further triturated in methanol to afford the title compound of Example 21 as a white solid (16.7 mg, 49% yield). 1H NMR (400 MHz, CHLOROFORM-D) δ ppm 7.57 (2H, d, J=8.28 Hz), 7.40 (2H, d, J=8.28 Hz), 7.08-7.20 (3H, m), 7.03 (2H, d, J=7.78 Hz), 6.96 (1H, s), 4.40 (1H, s), 3.94 (1H, d, J=16.31 Hz), 3.71-3.51 (6H, br m), 2.86 (1H, dd, J=7.15, 3.64 Hz), 1.82 (3H, s), 0.80-0.96 (2H, m), 0.59-0.71 (2H, m). LCMS m/z 614.2; HPLC Rt: 3.496 min. (Method A).

Examples 22-23

In a similar manner to Example 21, Step 2, Examples 22-23 were prepared via the amidation reactions of the acid of Example 21, Step 1 with 5-amino-N-isopropyl-1,3,4-thiadiazole-2-carboxamide and 5-methyl-1,3,4-thiadiazole-2-carboxamide, respectively. (All compounds are racemic.)

| Example | Structure R = | HPLC Rt minute (Method A) | LC MS [m/z] (M + H)] | 1H NMR (δ ppm) |
|---|---|---|---|---|
| 22 | 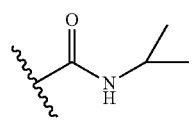 | 3.571 | 616.2 | (400 MHz, MeOD) 7.65 (2 H, d, J = 8.28 Hz), 7.41 (2 H, d, J = 8.28 Hz), 6.94-7.16 (6 H, m), 4.31 (1 H, s), 4.14 (m, 1H), 4.12 (1 H, d, J = 16.31 Hz), 3.73 (4 H, br m), 3.63 (2 H, br m), 3.49 (2 H, br m), 2.85 (1 H, d, J = 16.31 Hz), 1.79 (3 H, s), 1.25 (3 H, d, J = 1.76 Hz), 1.23 (3 H, d, J = 1.51 Hz) |

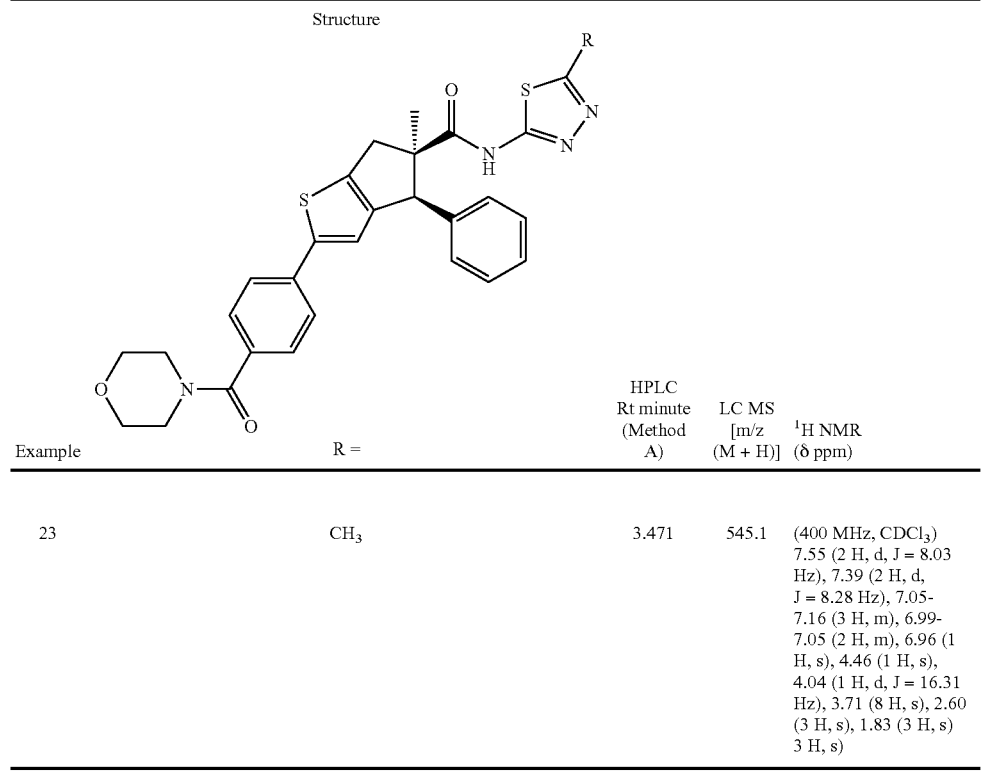
| Example | R = | HPLC Rt minute (Method A) | LC MS [m/z (M + H)] | $^1$H NMR (δ ppm) |
|---|---|---|---|---|
| 23 | CH$_3$ | 3.471 | 545.1 | (400 MHz, CDCl$_3$) 7.55 (2 H, d, J = 8.03 Hz), 7.39 (2 H, d, J = 8.28 Hz), 7.05-7.16 (3 H, m), 6.99-7.05 (2 H, m), 6.96 (1 H, s), 4.46 (1 H, s), 4.04 (1 H, d, J = 16.31 Hz), 3.71 (8 H, s), 2.60 (3 H, s), 1.83 (3 H, s) 3 H, s) |
Example 24
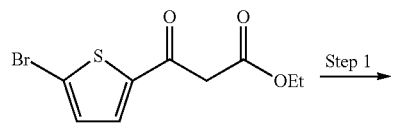 Step 1 →
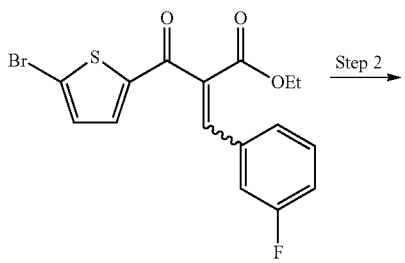 Step 2 →
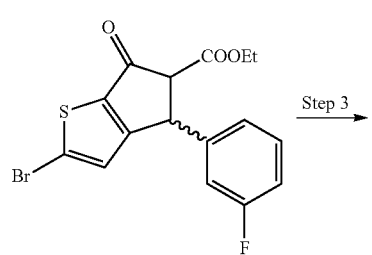 Step 3 →
-continued
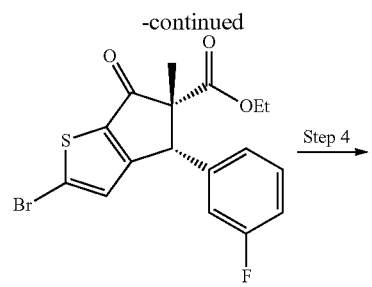 Step 4 →
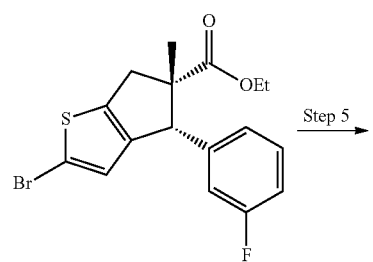 Step 5 →
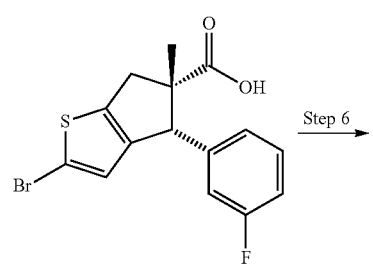 Step 6 →

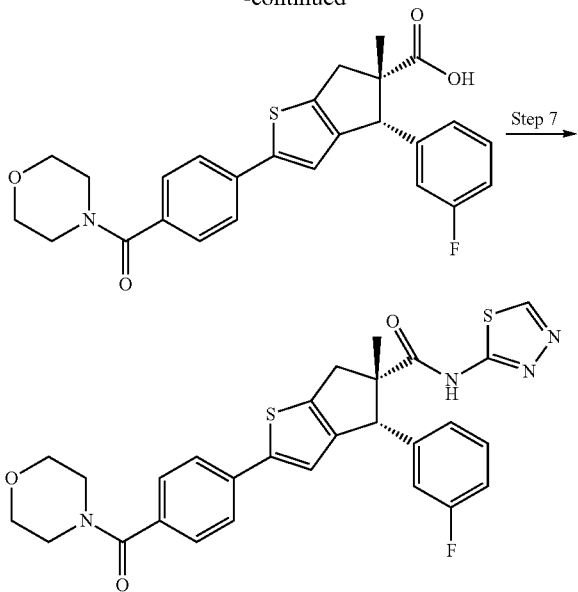

Step 1: Ethyl 2-(5-bromothiophene-2-carbonyl)-3-(3-fluorophenyl)acrylate

A solution of ethyl 3-(5-bromothiophen-2-yl)-3-oxopropanoate (2.456 g, 8.86 mmol, from Preparation 1, Step 1), 3-fluorobenzaldehyde (1.034 ml, 9.75 mmol), piperidine (0.088 ml, 0.886 mmol) and acetic acid (0.389 ml, 6.8 mmol) in benzene (50 ml) was heated at 85° C. for 6 h using a Dean-Stark trap to remove the formed water. The reaction solution was concentrated. The crude product was dissolved in a small amount of toluene and charged to 80 g silica gel cartridge which was eluted with a 15 min gradient from 0-5% ethyl acetate in hexane to give ethyl 2-(5-bromothiophene-2-carbonyl)-3-(3-fluorophenyl)acrylate as a viscous yellow oil (3.33 g). HPLC: Rt 3.728 min (Method A); LCMS m/z 407.02, 405.02 (M+23)

Step 2: Ethyl 2-bromo-4-(3-fluorophenyl)-6-oxo-5,6-dihydro-4H-cyclopenta[b]thiophene-5-carboxylate A solution of the product of Step 1 (3.25 g, 8.48 mmol) and Aluminium chloride (1.357 g, 10.18 mmol) in nitroethane (60 ml) was heated at 75° C. for 3 hours. The reaction mixture was poured into 1N HCl-ice solution, and extracted with DCM. The organic phase was washed with brine, dried (MgSO$^4$) and concentrated to give a brown liquid (3.06 g). The crude product was dissolved in a small amount of DCM and charged to a 120 g silica gel cartridge which was eluted with a 15 min gradient from 0-5% ethyl acetate in hexane to afford the enolate form of ethyl 2-bromo-4-(3-fluorophenyl)-6-oxo-5,6-dihydro-4H-cyclopenta[b]thiophene-5-carboxylate as a yellow viscous oil (1.631 g) and the keto-ester form of the product of Step 2 (1.17 g). LCMS m/z 385, 383; HPLC: Rt 3.725 min. (Method A)

Step 3: (Cis)-ethyl 2-bromo-4-(3-fluorophenyl)-5-methyl-6-oxo-5,6-dihydro-4H cyclopenta[b]thiophene-5-carboxylate A slurry suspension of the product of Step 2 (100 mg, 0.261 mmol), potassium carbonate (180 mg, 1.305 mmol) and iodomethane (0.098 ml, 1.566 mmol) in acetone (4 ml) was stirred at room temperature for 3.5 hours. The reaction mixture was taken into water and ethyl acetate. The organic phase was washed with brine, dried (MgSO$_4$) and concentrated to give yellow oil. The crude was purified via silica gel column (40 g silica gel cartridge with eluents of 0-4% ethyl acetate in hexane) to give (cis)-ethyl 2-bromo-4-(3-fluorophenyl)-5-methyl-6-oxo-5,6-dihydro-4H-cyclopenta[b]thiophene-5-carboxylate as a clear glass (325.7 mg, 68% yield). 1H NMR (400 MHz, MeOD) d ppm 7.28-7.45 (1H, m), 7.23 (4H, s), 6.98-7.10 (1H, m), 6.95 (1H, d, J=7.53 Hz), 6.79-6.88 (1H, m), 4.60 (1H, s), 3.56-3.72 (1H, m), 3.43-3.55 (1H, m), 1.65 (3H, s), 0.86 (3H, t, J=7.15 Hz); LCMS m/z 398.9; HPLC: Rt 3.535 min. (Method A).

Step 4: (Cis)-ethyl 2-bromo-4-(3-fluorophenyl)-5-methyl-5,6-dihydro-4H-cyclopenta[b]thiophene-5-carboxylate A solution of the product of Step 3 ((200 mg, 0.503 mmol), boron trifluoride etherate (3.19 ml, 25.2 mmol) and triethylsilane (3.22 ml, 20.14 mmol) in dichloromethane (6 ml) was stirred at room temperature for 70 h. The reaction mixture was treated with DMSO (1.608 ml, 22.66 mmol) at 0° C. and stirred at room temperature for 5 min. The reaction solution was taken into 1/1 Et2O-hexane and sat'd NaHCO3 solution. The organic phase was washed, dried and concentrated to give a clear oil. The crude product was dissolved in a small amount of toluene and charged to a 40 g silica gel cartridge which was eluted with 0-5% ethyl acetate in hexane to give (cis)-ethyl 2-bromo-4-(3-fluorophenyl)-5-methyl-5,6-dihydro-4H-cyclopenta[b]thiophene-5-carboxylate as a clear liquid (169 mg). 1H NMR (500 MHz, MeOD) δ ppm 7.17-7.29 (1H, m), 6.87-6.95 (1H, m), 6.79 (1H, d, J=7.70 Hz), 6.61-6.71 (2H, m), 4.13 (1H, s), 3.77 (1H, d, J=17.60 Hz), 3.65-3.72 (1H, m), 3.56-3.63 (1H, m), 2.74 (1H, d, J=16.50 Hz), 1.59 (3H, s), 0.90 (3H, t, J=7.15 Hz); HPLC: Rt 3.555 min (Method A).

Step 5: (Cis)-2-bromo-4-(3-fluorophenyl)-5-methyl-5,6-dihydro-4H-cyclopenta[b]thiophene-5-carboxylic acid A solution of the product of Step 4 (169 mg, 0.441 mmol), and 40% KOH aq. solution (3.0 ml) in DMSO (1.5 ml) and MeOH (4.0 ml) was stirred at 75° C. overnight. The reaction solution was concentrated. The residue was dissolved in water. The solution was adjusted to acidic with conc. HCl, and was extracted with ethyl ether. The organic phase was washed, dried (MgSO4) and evaporated to give (cis)-2-bromo-4-(3-fluorophenyl)-5-methyl-5,6-dihydro-4H-cyclopenta[b]thiophene-5-carboxylic acid as a white solid (144 mg, 92% yield). 1H NMR (400 MHz, MeOD) δ ppm 7.15-7.27 (1H, m), 6.85-6.93 (1H, m), 6.81 (1H, d, J=7.78 Hz), 6.68-6.74 (1H, m), 6.68 (1H, s), 4.11 (1H, d, J=1.00 Hz), 3.73 (1H, dd, J=16.19, 1.38 Hz), 2.73 (1H, d, J=16.31 Hz), 1.60 (3H, s); MS ES− m/z 355.2; HPLC Rt: 3.800 min (Method A).

Step 6: (Cis)-4-(3-fluorophenyl)-5-methyl-2-(4-(morpholine-4-carbonyl)phenyl)-5,6-dihydro-4H-cyclopenta[b]thiophene-5-carboxylic acid A solution of the product of Step 5 (90 mg, 0.253 mmol) and 2M potassium phosphate, dibasic (0.633 ml, 1.267 mmol) in DMF (2 ml) was purged with nitrogen for 10 minutes. To this solution was added tetrakis (triphenyl phosphine) palladium(0) (29.3 mg, 0.025 mmol). After purging with nitrogen for an additional 10 minutes, the reaction solution was heated at 113° C. for 0.5 hour. The product mixture was taken into ethyl ether and water. The organic phase was washed with sat'd NaHCO$_3$. The combined aqueous phase was adjusted to acidic with conc. HCl, and was extracted with ethyl acetate. The organic phase was washed (brine), dried (MgSO4) and concentrated to give the crude product which was purified via flash chromatography (12 g silica gel cartridge with eluents of 0-40% ethyl acetate in hexane to afford (cis)-4-(3-fluorophenyl)-5-methyl-2-(4-(morpholine-4-carbonyl)phenyl)-5,6-dihydro-4H-cyclopenta[b]thiophene-5-carboxylic acid as a white solid (75 mg, 64%). 1H NMR (400 MHz, MeOD) δ ppm 7.65 (2H, d, J=8.53 Hz), 7.41 (2H, d, J=8.53 Hz), 7.17-7.26 (1H, m), 7.06 (1H, s), 6.86-6.93 (2H, m), 6.74-6.79 (1H, m), 4.14 (1H, s), 3.82 (1H, d, J=16.56 Hz), 3.67 (4H, br m), 3.50 (2H, br m), 2.79 (1H, d, J=16.31 Hz), 1.64 (3H, s);); LCMS m/z 466.1 [M+1]; HPLC: Rt 3.853 min. (Method A)

Step 7: (Cis)-4-(3-fluorophenyl)-5-methyl-2-(4-(morpholine-4-carbonyl)phenyl)-N-(1,3,4-thiadiazol-2-yl)-5,6-dihydro-4H-cyclopenta[b]thiophene-5-carboxamide A solution of the product of Step 6 (22 mg, 0.047 mmol), HATU (27.0 mg, 0.071 mmol), 1,3,4-thiadiazol-2-amine (14.34 mg, 0.142 mmol) and DIPEA (0.050 mL, 0.284 mmol) in acetonitrile (2.5 mL) was heated at 70° C. for 15 h. The reaction mixture was diluted with methanol and purified via prep HPLC to afford the title compound of Example 24 (TFA salt) as a white solid (14.7 mg, 57% yield). 1H NMR (400 MHz, CDCl$_3$) δ ppm 8.70 (1H, s), 7.56 (2H, d, J=8.53 Hz), 7.39 (2H, d, J=8.53 Hz), 7.00-7.11 (1H, m), 6.95 (1H, s), 6.83 (1H, d, J=7.78 Hz), 6.74 (1H, td, J=12, 4 Hz), 6.68 (1H, dt, J=10.04, 1.76 Hz), 4.53-4.56 (1H, m), 4.09 (1H, d, J=16.31 Hz), 2.94 (1H, d, J=16.31 Hz), 1.85 (3H, s); LCMS m/z 549.3; HPLC: Rt 3.456 min. (Method A).

Examples 25-26

In a similar manner to Example 24, Step 7, Examples 25-26 were prepared via the amidation reactions of the acid of Example 24, Step 6 with 5-amino-N-isopropyl-1,3,4-thiadiazole-2-carboxamide and 5-amino-N-cyclopropyl-1,3,4-thiadiazole-2carboxamide, respectively. (All compounds are racemic.)

| Example | R = | HPLC Rt minute (Method A) | LC MS [m/z (M + H)] | $^1$H NMR (δ ppm) |
|---|---|---|---|---|
| 25 | 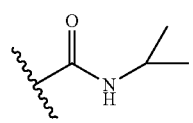 | 3.738 | 634.2 | (400 MHz, CDCl$_3$) 9.76 (1 H, s), 7.57 (2 H, d, J = 8.28 Hz), 7.41 (2 H, d, J = 8.53 Hz), 7.04-7.16 (1 H, m), 6.90-6.97 (2 H, m), 6.83 (1H, d, J = 8 Hz), 6.81-6.85 (1 H, m), 6.77-6.82 (1 H, m), 3.73 (6 H, s), 3.01 (1 H, d, J = 16.56 Hz), 1.82 (3 H, s), 1.26 (3 H, s), 1.25 (3 H, s). |

Biological Activity Data

The AP-1 activity of Examples 1 to 26 is given where the AP-1 $EC_{50}$ is less than 1 uM. Accompanying AP-1 maximum inhibition values are also given. Where the AP-1 $EC_{50}$ is greater than 1 uM and/or the maximal inhibition is less than 20%, the glucocorticoid receptor (GR) binding affinity (Ki) is given.

The data presented below were obtained using the assays referred to in the table and described herein in the ASSAY section supra.

| Example | GR (Ki, nM) (GR Binding Assay) (I)[a] | AP-1 $EC_{50}$, nM (Cellular Trans-repression Assay) | AP-1 Max % inh (Cellular Trans-repression Assay) |
|---|---|---|---|
| 1 | 5.30 | | |
| 2 | 5.34 | | |
| 3 | 1.80 | | |
| 4 | | 35.04 | 52.82 |
| 5 | | 13.98 | 43.98 |
| 6 | | 53.12 | 29.32 |
| 7 | | 22.47 | 44.81 |
| 8 | | 42.15 | 42.74 |
| 9 | | 40.22 | 26.03 |
| 10 | | 24.23 | 27.94 |
| 11 | 1.90 | | |
| 12 | | 29.10 | 43.11 |
| 13 | | 23.88 | 50.68 |
| 14 | | 63.74 | 42.02 |
| 15 | | 18.84 | 53.20 |
| 16 | | 289.60 | 56.78 |
| 17 | | 365.00 | 40.26 |
| 18 | | 27.34 | 29.81 |
| 19 | | 21.76 | 38.78 |
| 20 | 3.37 | | |
| 21 | | 22.77 | 60.04 |
| 22 | | 34.50 | 55.76 |
| 23 | | 452.20 | 29.00 |
| 24 | | 23.08 | 37.80 |
| 25 | | 55.77 | 44.50 |
| 26 | | 148.40 | 45.28 |

What is claimed is:

1. A compound according to Formula I

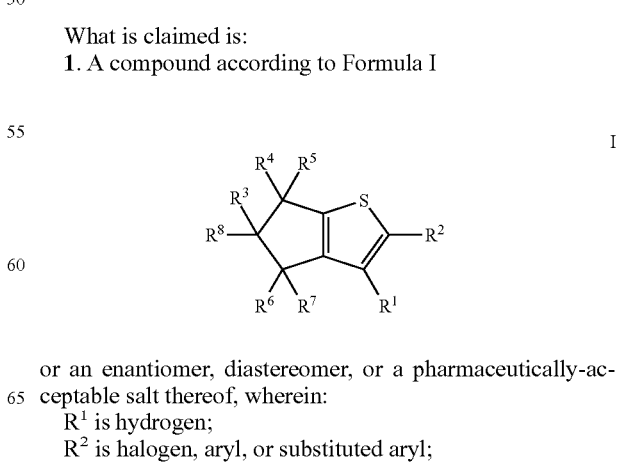

or an enantiomer, diastereomer, or a pharmaceutically-acceptable salt thereof, wherein:
$R^1$ is hydrogen;
$R^2$ is halogen, aryl, or substituted aryl;

R³ is alkyl;
R⁴ and R⁵ are each H;
R⁶ is aryl or substituted aryl;
R⁷ is H;
R⁸ is R⁹—NH—C(=O); and
R⁹ is an optionally substituted thiadiazolyl group.

2. A compound of claim 1, wherein R² is selected from the group consisting of: halogen or substituted aryl.

3. A compound of claim 1, wherein R² is selected from the group consisting of: unsubstituted phenyl and phenyl substituted with one to two groups selected from halogen, morpholin-1-ylcarbonyl, pyrrolidin-1-ylcarbonyl, N-methyl-N-ethylaminocarbonyl, 3-fluoropyrrolidin-1-ylcarbonyl, 3,3-difluoropyrrolidin-1-ylcarbonyl and N,N-dimethylaminocarbonyl.

4. A compound according to any one of claim 1 or 2, wherein R² is a halogen.

5. A compound according to any one of claim 1, 2 or 3, wherein R⁸ is R⁹—NH—C(=O) where R⁹ is optionally substituted

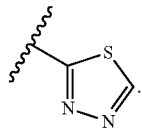

6. A compound according to any one of claim 1 or 2, wherein:
R² is halogen or phenyl substituted with one to two groups selected from halogen, (optionally substituted 5- to 7-membered heterocyclo)carbonyl and (lower alkyl)₁₋₂ aminocarbonyl;
R³ is lower alkyl; and
R⁶ is optionally substituted phenyl, wherein the optionally substituted substituents are selected from the group consisting of: halogen, lower alkyl, cyano, CF₃, (lower alkyl)amino, cyano, (lower alkyl)sulfonyl and carboxamide.

7. A compound according to any one of claim 1, 2 or 3, wherein:
R² is phenyl substituted with one to two groups selected from halogen, morpholin-1-ylcarbonyl, pyrrolidin-1-ylcarbonyl, N-methyl-N-ethylaminocarbonyl, 3-fluoropyrrolidin-1-ylcarbonyl, 3,3-difluoropyrrolidin-1-ylcarbonyl and N,N-dimethylaminocarbonyl;
R³ is lower alkyl;
R⁴ is hydrogen;
R⁵ is hydrogen;
R⁶ is phenyl or phenyl substituted with a halogen;
R⁷ is hydrogen; and
R⁹ is 1,3,5-thidiazol-2-yl, 1,3,4-thiadiazol-2-yl or thiazol-2-yl, each group optionally substituted with one to two groups selected from halogen, lower alkyl, cyano, CF₃, (lower alkyl)amino, cyano, (lower alkyl)sulfonyl, (C₃₋₅ cycloalkyl)carboxamide, or (lower alkyl)₁₋₂carboxamide.

8. A compound according to any one of claim 1, 2 or 3, wherein:
R² is phenyl substituted in the 4-position with morpholin-1-ylcarbonyl, pyrrolidin-1-ylcarbonyl, N-methyl-N-ethylaminocarbonyl, 3-fluoropyrrolidin-1-ylcarbonyl, 3,3-difluoropyrrolidin-1-ylcarbonyl or N,N-dimethylaminocarbonyl, and optionally, halogen.

9. A pharmaceutical composition comprising at least one compound according to claim 1 and a pharmaceutically-acceptable carrier.

10. A combination of a compound according to any one of claim 1, 2 or 3 and one or more compounds selected from an immunosuppressant, an anticancer agent, an anti-viral agent, an anti-inflammatory agent, an anti-fungal agent, an antibiotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

* * * * *